United States Patent [19]
McFarland et al.

[11] Patent Number: 6,096,412
[45] Date of Patent: Aug. 1, 2000

[54] HIGH COLOR DENSITY PRINTING ON SANITARY DISPOSABLE PAPER PRODUCTS EXHIBITING RESISTANCE TO INK RUB-OFF

[75] Inventors: James Robert McFarland; Arman Ebrahimpour; Nicholas James Nissing, all of Cincinnati, Ohio

[73] Assignee: The Procter & Gamble Company, Cincinnati, Ohio

[21] Appl. No.: 09/130,615

[22] Filed: Aug. 7, 1998

[51] Int. Cl.[7] .................................................. B32B 3/00
[52] U.S. Cl. ........................ 428/211; 428/500; 428/507; 428/511; 428/514
[58] Field of Search ...................................... 428/211, 500, 428/507, 511, 514; 106/31.13

[56] References Cited

U.S. PATENT DOCUMENTS

| | | | |
|---|---|---|---|
| 3,642,502 | 2/1972 | Schneider | 106/23 |
| 3,950,290 | 4/1976 | Drury, Jr. et al. | 260/23 |
| 4,420,583 | 12/1983 | Hutton | 524/501 |
| 4,495,323 | 1/1985 | Collins | 524/426 |
| 5,158,606 | 10/1992 | Carlick et al. | 524/145 |
| 5,173,111 | 12/1992 | Krishnan et al. | 106/20 |
| 5,221,699 | 6/1993 | Nachfolger et al. | 523/402 |
| 5,314,043 | 5/1994 | Steinwand | 524/501 |
| 5,373,045 | 12/1994 | Smith et al. | 524/385 |
| 5,458,590 | 10/1995 | Schleinz et al. | 604/361 |
| 5,494,759 | 2/1996 | Williams et al. | 428/514 |
| 5,498,661 | 3/1996 | Hutter | 524/753 |
| 5,569,529 | 10/1996 | Becker et al. | 428/331 |
| 5,612,118 | 3/1997 | Schleinz et al. | 428/195 |

FOREIGN PATENT DOCUMENTS

| | | | |
|---|---|---|---|
| WO 97/03138 | 1/1997 | WIPO | C09D 11/10 |
| WO 97/18090 | 5/1997 | WIPO | B41M 5/00 |
| WO 97/40108 | 10/1997 | WIPO | C09D 11/00 |
| WO 97/44195 | 11/1997 | WIPO | B41M 3/00 |

*Primary Examiner*—William Krynski
*Assistant Examiner*—Hong J. Xu
*Attorney, Agent, or Firm*—Julia A. Glazer; Larry L. Huston; Donald E. Hasse

[57] ABSTRACT

Disclosed is a sanitary disposable paper product having improved resistance to ink rub-off. Also disclosed is a sanitary disposable paper product having high color density print characteristics which exhibits improved resistance to ink rub-off. The sanitary disposable paper product comprises a fibrous sheet containing cellulose wherein the ink is applied to at least one surface of the paper.

33 Claims, 11 Drawing Sheets

HIGH COLOR DENSITY PRINTING ON SANITARY DISPOSABLE PAPER PRODUCTS EXHIBITING RESISTANCE TO INK RUB-OFF

FIELD OF THE INVENTION

This invention relates to a sanitary disposable paper product having inks with improved resistance to ink rub-off. Also disclosed is a sanitary disposable paper product having high color density print characteristics while exhibiting improved resistance to ink rub-off.

BACKGROUND OF THE INVENTION

Applying images to paper products by utilizing pigment based ink compositions is well known in the art. One of the difficulties historically experienced with sanitary disposable paper products (including facial tissue, bath tissue, table napkins, wipes, and cotton pads) printed with pigment based ink compositions is the tendency for the ink to rub-off of the surface of the paper upon exposure of the paper to liquids. The problem is even more pronounced for those sanitary disposable paper products printed with inks exhibiting relatively high color densities.

The tendency for the ink to rub-off increases as the printed sanitary disposable paper product is exposed to liquids such as tap water. Furthermore, exposing the sanitary disposable paper product printed with ink to common household cleaning products containing solventized alkaline liquids, or acid-containing cleaning liquids tends to increase ink rub-off as compared to exposure of the paper towelling to tap water alone.

U.S. Pat. No. 3,642,502 issued to Schneider on Feb. 15, 1972 teaches a bleed resistant ink composition comprising a coloring material, polyamide epichlorohydrin, talc, and a solvent for printing on paper products.

This teaching neither addresses sanitary disposable paper products having high color density images, nor does it address images produced from water-based pigment containing ink compositions which exhibit resistance to ink rub-off.

The benefit of the present invention is the ability to provide a sanitary disposable paper product exhibiting high color density images while exhibiting resistance to ink rub-off. A further benefit of the present invention is the ability to provide a sanitary disposable paper product which exhibits high color density images while exhibiting resistance to ink rub-off upon exposure to a wide variety of liquids across a broad pH range including but not limited to water and common household cleaners such as alkaline-based, solvent-based, surfactant-based, and acid-based cleaners. Yet a further benefit of the present invention is the ability to provide a sanitary disposable paper product which exhibits resistance to ink rub-off without requiring the addition of a separate prophylactic coating over the ink.

SUMMARY OF THE INVENTION

This invention relates to a sanitary disposable paper product comprising a fibrous sheet containing cellulose. The fibrous sheet has a first outer surface and a second outer surface opposed to the first outer surface. An ink is disposed on at least one of the surfaces. The ink has a Sigma $\Delta E$ which is a function of color density of the ink. For inks exhibiting a dominant primary color of black, Sigma $\Delta E$ is defined by the inequality: $y(x) \leq 75.041 - 260.72x + 275.27x^2 - 70.158x^3 - 6.9911x^4$, wherein $0.8 \leq x \leq 1.4$, and $y(x) \leq 3$, wherein $0.5 \leq x < 0.8$.

Preferably for inks exhibiting a dominant primary color of black, Sigma $\Delta E$ is defined by the inequality: $y(x) \leq 73.041 - 260.72x + 275.27x^2 - 70.158x^3 - 6.9911x^4$, wherein $0.8 \leq x \leq 1.4$, and $y(x) \leq 2$, wherein $0.5 \leq x < 0.8$.

For process inks exhibiting a dominant primary color of black, Sigma $\Delta E$ is defined by the inequality: $y(x) \leq 75.041 - 260.72x + 275.27x^2 - 70.158x^3 - 6.9911x^4$, wherein $0.8 \leq x \leq 1.4$, and $y \leq 3$, wherein $0.5 \leq x < 0.8$. Preferably for process inks exhibiting a dominant primary color of black, Sigma $\Delta E$ is defined by the inequality: $y(x) \leq 74.041 - 260.72x + 275.27x^2 - 70.158x^3 - 6.9911x^4$, wherein $0.8 \leq x \leq 1.4$, and $y \leq 2$, wherein $0.5 \leq x < 0.8$.

For inks exhibiting a dominant primary color of cyan, Sigma $\Delta E$ is defined by the inequality: $y(x) \leq -593.36 + 2340.1x - 3350x^2 + 2073.8x^3 - 465.5x^4$, wherein $0.7 \leq x \leq 1.50$. Preferably for inks exhibiting a dominant primary color of cyan, Sigma $\Delta E$ is defined by the inequality: $y(x) \leq -595.36 + 2340.1x - 3350x^2 + 2073.8x^3 - 465.5x^4$, wherein $0.7 \leq x \leq 1.50$.

For process inks exhibiting a dominant primary color of cyan, Sigma $\Delta E$ is defined by the inequality: $y(x) \leq 57.701 - 222.16x + 268.91x^2 - 87.964x^3$, wherein $0.5 \leq x \leq 1.5$. Preferably for process inks exhibiting a dominant primary color of cyan, Sigma $\Delta E$ is defined by the inequality: $y(x) \leq 55.701 - 222.16x + 268.91x^2 - 87.964x^3$, wherein $0.5 \leq x \leq 1.5$.

For inks exhibiting a dominant primary color of magenta, Sigma $\Delta E$ is defined by the inequality: $y(x) \leq -1549.8 + 12473x - 40898x^2 + 69923x^3 - 65676x^4 + 32126x^5 - 6391.7x^6$, wherein $0.5 \leq x < 1.2$, and $y(x) \leq 22$, wherein $1.2 \leq x \leq 1.4$. Preferably for inks exhibiting a dominant primary color of magenta, Sigma $\Delta E$ is defined by the inequality: $y(x) \leq -1551.8 + 12473x - 40898x^2 + 69923x^3 - 65676x^4 + 32126x^5 - 6391.7x^6$, wherein $0.7 \leq x < 1.2$, and $y(x) \leq 16$, wherein $1.2 \leq x \leq 1.4$.

For process inks exhibiting a dominant primary color of magenta, Sigma $\Delta E$ is defined by the inequality: $y(x) \leq -50.197 + 265.12x - 490.01x^2 + 398.49x^3 - 112.31x^4$, wherein $0.5 \leq x \leq 1.4$. Preferably for process inks exhibiting a dominant primary color of magenta, Sigma $\Delta E$ is defined by the inequality: $y(x) \leq -52.197 + 265.12x - 490.01x^2 + 398.49x^3 - 112.31x^4$, wherein $0.5 \leq x \leq 1.4$.

For inks exhibiting a dominant primary color of yellow, Sigma $\Delta E$ is defined by the inequality: $y(x) \leq -2103.34 + 10184.4x - 18237x^2 + 14346.4x^3 - 4175.14x^4$, wherein $0.7 \leq x \leq 1.0$, and $y(x) \leq 4$, wherein $0.5 \leq x < 0.7$. Preferably for inks exhibiting a dominant primary color of yellow, Sigma $\Delta E$ is defined by the inequality: $y(x) \leq -2105.34 + 10184.4x - 18237x^2 + 14346.4x^3 - 4175.14x^4$, wherein $0.7 \leq x < 1.0$, and $y(x) \leq 14$, wherein $1.0 \leq x \leq 1.2$, and $y(x) \leq 2$, wherein $0.5 \leq x < 0.7$.

For process inks exhibiting a dominant primary color of yellow, Sigma $\Delta E$ is defined by the inequality: $y(x) \leq 90.549 - 332.78x + 422.27x^2 - 158.5x^3$, wherein $0.7 \leq x < 1.3$. Preferably for process inks exhibiting a dominant primary color of yellow, Sigma $\Delta E$ defined by the inequality: $y(x) \leq 86.549 - 332.78x + 422.27x^2 - 158.5x^3$, wherein $0.7 \leq x < 1.3$.

Binders used in the ink compositions of this invention include: acrylic emulsion polymers, polyurethane dispersions, ethylene vinyl acetate emulsions, and styrene butadiene latex emulsions. The binders are film-forming polymers having a molecular weight of at least about 500,000 and a $T_g$ of less than about 100° C. It is desirable that the binders crosslink. It is also desirable that the binders be non-carboxylated.

The inks used in this invention typically have a binder solids to pigment solids ratio between about 0.10:1 to 3:1. The solubility of ink films formed from the ink compositions of this invention typically have a solubility in distilled deionized water or a solubility in a solventized alkaline solution of no more than about 85 milligrams of dissolved ink pigment per gram of dry ink film. The ink films typically have a toughness (measured at 50% strain) of at least about 0.01 MPa and a maximum strain of at least about 0.3.

The ink compositions of this invention may include glycerin. They may also include wax.

DETAILED DESCRIPTION OF THE INVENTION

Figure 1:
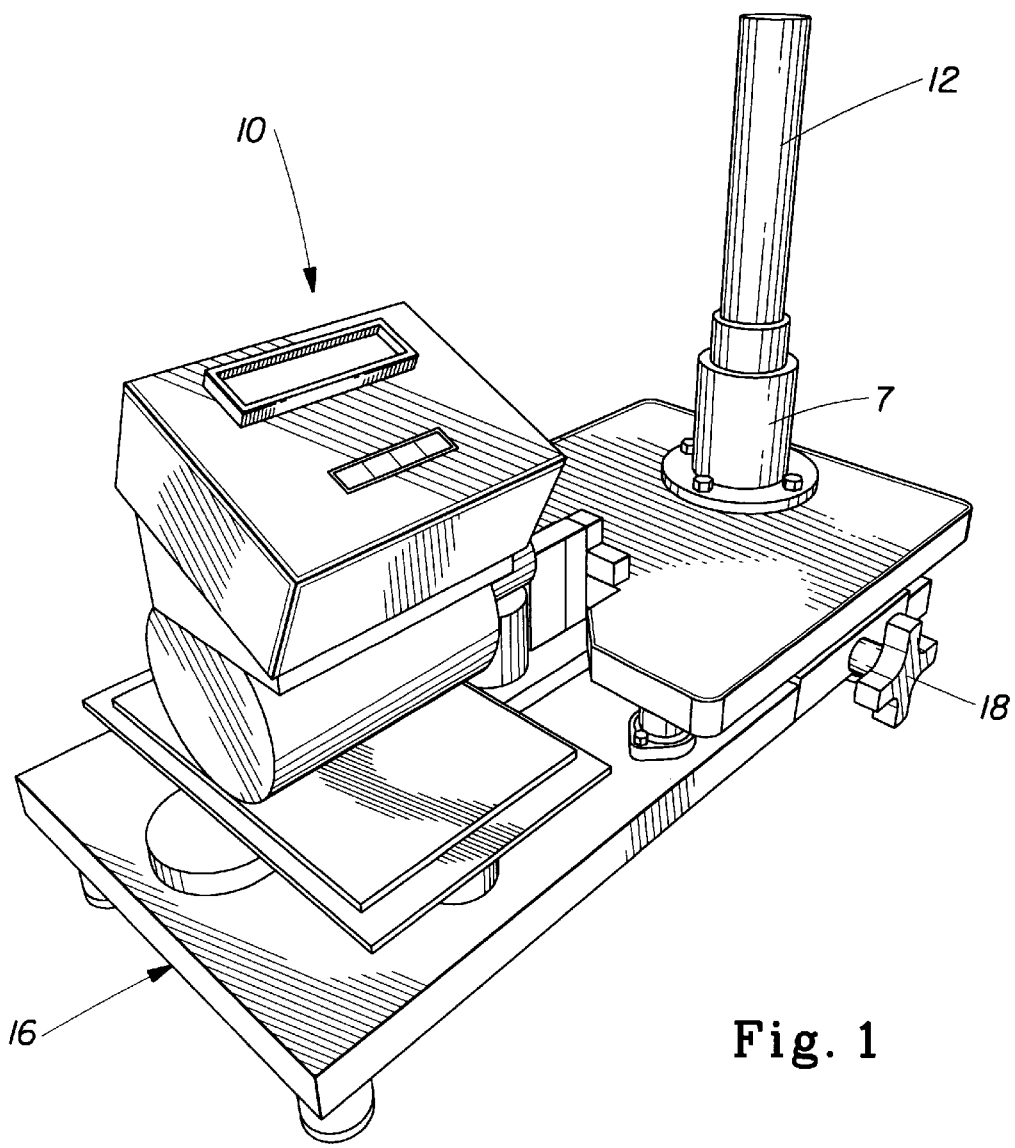
FIG. 1 is a front perspective view of an ink rub tester for generating ink rub-off data.

In order to enhance the aesthetics of sanitary disposable paper products, it is desirable to use pigment based inks which produce vibrant high color densities when applied to the sanitary disposable paper product. As used herein, "color density" may be defined by the following equation:

$$D = \log_{10} I/R$$

wherein I, refers to the intensity of incident light, and R, refers to the intensity of reflected light.

One method of producing color images entails applying pigment based ink compositions to the surface of the paper. However, as color density increases, the tendency for ink to rub off of the paper also increases.

As used herein, "rub-off" refers to the transfer of color from the surface of a printed substrate to another surface. Rub-off is composed of two components, bleed and abrasion. Bleed refers to the tendency of color to leach out of a substrate upon exposure of the substrate to a liquid. Abrasion refers to the ability to remove ink from a substrate by mechanically scuffing the ink from the surface of the substrate.

The present invention relates to a sanitary disposable paper product comprising a fibrous sheet containing cellulose and an ink composition applied thereon. The individual components of the ink composition may be applied to the fibrous sheet as a mixture or sequentially. The paper product of this invention provides improved resistance to ink rub-off without having to apply a separate prophylactic coating to the fibrous sheet.

Preferably the fibrous sheet is a sanitary disposable paper product, such as tissue, having a basis weight of about 8 lbs/3000 ft$^2$ to 50 lbs/3000 ft$^2$. The fibrous sheet of this invention has a first outer surface and a second outer surface wherein the second outer surface is oppositely disposed to the first outer surface. Ink is applied to at least one of the first and second outer surfaces. The fibrous sheet of this invention may be made according to commonly assigned U.S. Patents: U.S. Pat. No. 4,191,609 issued Mar. 4, 1980 to Trokhan; U.S. Pat. No. 4,300,981 issued to Carstens on Nov. 17, 1981; U.S. Pat. No. 4,191,609 issued to Trokhan on Mar. 4, 1980; U.S. Pat. No. 4,514,345 issued to Johnson et al. on Apr. 30, 1985; U.S. Pat. No. 4,528,239 issued to Trokhan on Jul. 9, 1985; U.S. Pat. No. 4,529,480 issued to Trokhan on Jul. 16, 1985; U.S. Pat. No. 4,637,859 issued to Trokhan on Jan. 20, 1987; U.S. Pat. No. 5,245,025 issued to Trokhan et al. on Sep. 14, 1993; U.S. Pat. No. 5,275,700 issued to Trokhan on Jan. 4, 1994; U.S. Pat. No. 5,328,565 issued to Rasch et al. on Jul. 12, 1994; U.S. Pat. No. 5,334,289 issued to Trokhan et al. on Aug. 2, 1994; U.S. Pat. No. 5,364,504 issued to Smurkowski et al. on Nov. 15, 1995; U.S. Pat. No. 5,527,428 issued to Trokhan et al. on Jun. 18, 1996; U.S. Pat. No. 5,556,509 issued to Trokhan et al. on Sep. 17, 1996; U.S. Pat. No. 5,628,876 issued to Ayers et al. on May 13, 1997; U.S. Pat. No. 5,629,052 issued to Trokhan et al. on May 13, 1997; and U.S. Pat. No. 5,637,194 issued to Ampulski et al. on Jun. 10, 1997, the disclosures of which are incorporated herein by reference for the purpose of showing how to make a fibrous sheet suitable for use with the present invention.

The fibrous sheet may also be made according to U.S. Pat. No. 5,411,636 issued to Hermans et al. on May 2, 1995 and EP 677612 published in the name of Wendt et al. on Oct. 18, 1995.

The fibrous sheet of the present invention may be through air dried or conventionally dried. Optionally, it may be foreshortened by creping or by wet microcontraction. Creping and wet microcontraction are disclosed in commonly assigned U.S. Patents: U.S. Pat. No. 4,440,597 issued to Wells et al. on Apr. 3, 1984 and U.S. Pat. No. 4,191,756 issued to Sawdai on May 4, 1980, the disclosures of which patents are incorporated herein by reference.

Though the primary use of the present invention is in connection with toweling, the inks are also applicable to other sanitary disposable paper products including but not limited to: facial tissue, bath tissue, table napkins, wipes and cotton pads. The fibrous sheet may be composed of materials which are cellulosic, noncellulosic, or a combination thereof.

The ink composition of the present invention is any liquid composition which may be applied onto the fibrous sheet in a predetermined pattern.

Components of the ink composition of the present invention may include but are not limited to: a vehicle such as a solvent or water; a colorant such as a pigment; a binder; and other components which may include but are not limited to wax, crosslinking agents, pH control agents, viscosity modifiers, defoamers, dispersants, printing press hygiene control agents, preservatives, and corrosion control agents.

As used herein, "ink" refers to any liquid composition or components thereof applied to the fibrous sheet and which remains thereon in a visible pattern even though components of the ink may evaporate. The components of the ink composition may be applied to the fibrous sheet sequentially or as a mixture. A "predetermined pattern" or "image" refers to any desired array or application of ink onto the fibrous sheet and is inclusive of all combinations of patterns ranging from small individual dots to complete coating of the entire surface of the substrate. As used herein, "vehicle" refers to the liquid component of the ink composition utilized to convey the ink composition to the surface of the fibrous sheet. As used herein, "pigment" refers to insoluble color matter used in finely divided dispersed form to impart color to the ink. As used herein, "binder" refers to the adhesive component of the ink composition.

Suitable ink compositions of the present invention include but are not limited to those ink compositions that are in the form of a liquid at room temperature (i.e.; a temperature of about 20° C.). The ink compositions will preferably utilize water as a vehicle and pigment as a colorant.

Though the pigments described and used herein, are organic pigments, particularly Diarylide Yellow 14, Rubine Magenta Red 238, Phthalocyan Blue 15:3, and Carbon Black 7, it is understood that the ink compositions of the present invention could be extended to include inorganic pigments as well as other organic pigments. Smaller pigment particle sizes are preferred over relatively larger size pigment particles. The pigment of the present invention preferably has a particle size of less than 5 microns, more preferably less than 1 micron, and even more preferably less than 0.5 microns.

A binder is needed for the ink to adhere to the surface of the fibrous sheet. In general, rub-off resistance of the ink composition increases as adherence of the ink to the surface of the fibrous sheet increases. Ink compositions which include binders comprised of film-forming polymers tend to have improved adherence of the ink to the surface of the fibrous sheet in comparison to inks containing non film-forming binders. A film-forming polymer tends to form a film at a temperature above its glass transition temperature. As used herein, "film-forming" refers to a material which forms a tough continuous film above the $T_g$ of the material. As used herein, "toughness" refers to a measure of the amount of energy absorbed by a material as a tensile stress is placed upon it. Toughness, indicated by the area under the material's tensile stress-strain curve, may be ascertained by the following equation:

$$T = \int_0^{0.5} \sigma d\varepsilon$$

wherein T, indicates toughness for the test conditions described herein, $\sigma$, represents stress, and $\varepsilon$, represents the strain. Strain, $\varepsilon$, is defined as:

$\varepsilon$=[(length of stretched film–length of film before stretching)/ length of film before stretching]

As used herein, toughness is calculated up to a strain of 0.5. Based on the above equation, a toughness measured at 50% strain, indicates that the toughness is calculated up to the point at which the film has been stretched to 1.5 times its original length.

Suitable binders used for the present invention are film-forming polymers having a molecular weight of at least about 200,000, preferably of at least about 1,000,000 and a glass transition temperature ($T_g$) of less than about 100° C., preferably less than about 30° C., and more preferably less than about 0° C. The binder is preferably nonionic or anionic and is preferably stabilized with surfactant. Film-forming polymers which may be used as binders in the ink compositions of the present invention include: preferably acrylic emulsion polymers, more preferably polyurethane dispersions and ethylene vinyl acetate emulsions, and most preferably styrene butadiene latex emulsions.

The most preferred styrene butadiene latex emulsion is a non-carboxylated, film-forming polymer having a $T_g$ of about –20° C., having a solids content of about 45% to 50% based upon weight, and a molecular weight of at least about 500,000. Though the most preferred styrene butadiene latex emulsion is non-carboxylated, it should be noted that carboxylated styrene butadiene latex emulsions are included within the scope of this invention.

As used herein "non-carboxylated" refers to a polymer which is not purposefully enriched with carboxyl units. Thus, if a carboxyl unit is present, it is only present as a functional group in the polymer backbone.

The preferred acrylic emulsion polymer is non-carboxylated and nonionic having a $T_g$ of about –10° C. The preferred acrylic emulsion polymer has a solids content of approximately 45% based on weight, and a molecular weight of at least about 500,000. The preferred acrylic emulsion polymer which is comprised of about 96% ethyl acrylate and about 4% or less methylol acrylamide is stabilized with about 6% by weight of an alkyl phenol ethoxylate surfactant. The preferred acrylic emulsion polymer crosslinks at a temperature of about 135° C. A preferred acrylic emulsion polymer is sold as RHOPLEX NW2744 available from Rohm & Haas of Philadelphia, Pa.

A preferred polyurethane dispersion which may be used as a binder in the ink composition of the present invention is an aliphatic polyurethane dispersion which includes urea and ester functionalities in the polymer backbone. The preferred polyurethane dispersion has a $T_g$ of about –30° C. The preferred polyurethane dispersion is anionic, having a molecular weight of at least about 400,000 and a solids content of about 30% based on weight. A preferred polyurethane dispersion is commercially sold as WITCOBOND W-234 available from Witco Corporation of Greenwich, Conn.

The preferred ethylene vinyl acetate emulsion has a molecular weight of at least about 500,000. The preferred ethylene vinyl acetate emulsion has a $T_g$ of preferably 10° C. or less, more preferably a $T_g$ of –15° C. or less, and a solids content of about 50% based upon weight. The preferred ethylene vinyl acetate emulsion crosslinks when heated to a temperature of about 100° C. to 135° C. The crosslinking is accomplished by incorporating methyl acrylamide functionality into the polymer backbone. Preferred ethylene vinyl acetate emulsion polymers which may be used as binders in the ink composition of the present invention are commercially sold as AIRFLEX 124 and AIRFLEX 192, available from Air Products and Chemicals, Inc. of Allentown, Pa.

Properties of the preferred binders are summarized in Table I.

TABLE I

PROPERTIES OF PREFERRED BINDERS

| BINDER TYPE | FILM-FORMING | APPROX. $T_1$ (° C.) | CROSS-LINKING | CARBOXY-LATED |
|---|---|---|---|---|
| STYRENE BUTADIENE LATEX EMULSION | YES | −20 | NO | NO |
| ACRYLIC EMULSION | YES | −10 | YES | NO |
| POLYURETHANE DISPERSION | YES | −30 | NO | YES |
| ETHYLENE VINYL ACETATE EMULSION | YES | −15 | YES | NO |
| ETHYLENE VINYL ACETATE EMULSION | YES | +10 | YES | NO |

The raw ink composition of the present invention has a Shell Cup viscosity at a temperature of 20° C. of preferably about 200 centipoises or less, more preferably about 70 centipoises or less, and most preferably about 25 centipoises or less. As used herein, "raw ink" refers to the ink composition prior to the application process in which it is applied to the substrate. As is well known in the art, a #1 Shell Cup is used to measure viscosities which range from about 1 centipoise to 10 centipoise. A #2 Shell Cup is used to measure viscosities which range from about 7.5 centipoise to 30 centipoise. A #3 Shell Cup is used to measure viscosities which range from about 25 centipoise to 80 centipoise and a #4 Shell Cup is used to measure viscosities which range from about 60 centipoise to 200 centipoise.

The ink compositions of the present invention have a pH in the range of about 2–11 and preferably about 7–10. A typical ink composition used in conjunction with the present invention has a binder solids to pigment solids ratio of from about 0.10:1 to 3:1, preferably about 0.5:1 to 2:1, and more preferably about 1.0:1 to 1.5:1. A surfactant(s) or dispersant(s) may be added to the ink composition to disperse the binder and pigment.

To improve ink rub-off resistance, the ink composition of this invention may contain a wax. A wax suitable for this invention includes but is not limited to a polyethylene wax emulsion. Addition of a wax to the ink composition of the present invention enhances rub resistance by setting up a barrier which inhibits the physical disruption of the ink film after application of the ink to the fibrous sheet. Based on weight percent solids of the total ink composition, suitable addition ranges for the wax are from about 0.5% solids to 10% solids. An example of a suitable polyethylene wax emulsion is JONWAX 26 supplied by S.C. Johnson & Sons, Inc. of Racine, Wis.

A non-limiting list of optional additives which may be added to the finished ink compositions of the present invention include crosslinking agents, printing press hygiene control agents, humectants, corrosion control agents, pH control agents, viscosity modifiers, preservatives, and defoamers.

Crosslinking agents are generally added to the finished ink composition or to a pigment dispersion. As used herein, "finished ink composition" refers to an ink composition that contains the key components such as a vehicle, pigment, and binder so as to render the ink composition ready to use. As used herein, "pigment dispersion" refers to a composition comprised of pigment solids, surfactant, and a vehicle such as water or oil to which a binder is added.

Crosslinking agents are believed to enhance the rub-off resistance of the ink by crosslinking with the ink. A non-limiting example of a suitable crosslinking agent, is a solution polymer of a cationic polyamine-epichlorohydrin polymer. Based upon weight percent of the total ink composition, suitable addition ranges for the crosslinking agent are from about 3% to 15%, and preferably from about 4% to 8% (based on the solids content of the crosslinking agent). A preferred crosslinking agent is KYMENE PLUS available from Hercules Inc. of Wilmington, Del.

Glycerin may also be added to the ink composition of the present invention in order to improve rub-off resistance. Based upon weight percent of the total ink composition, suitable addition ranges for the glycerin range from about 0.5% to 20%, preferably from about 3% to 15%, and more preferably from about 8% to 13%.

Methods of curing the inks of the present invention include but are not limited to thermally curing, electron beam curing, photon curing (for example ultraviolet light, x-ray, and gamma ray), and combinations thereof.

The properties of preferred ink compositions useful with the present invention are summarized in Table II. Referring to Table II, column 1 indicates the pigment type and color. Column 2 indicates the weight percentage of pigment solids contained within the ink composition. Column 3 indicates the type of binder contained within the ink composition. Column 4 indicates the approximate $T_g$ of the binder contained within the ink composition. Column 5 indicates the weight percentage of binder solids contained within the ink composition. Column 6 indicates the ratio of binder solids to pigment solids contained within the ink. Column 7 indicates the vehicle used in the ink composition. Column 8 indicates whether the ink composition includes wax. Column 9 indicates what type of crosslinking agent (if any) is added to the finished ink composition. Column 10 indicates the amount of the crosslinking agent (based on solids content of the crosslinking agent) from column 8 added to the finished ink composition.

TABLE II

PROPERTIES OF PREFERRED INK COMPOSITIONS

| (1) PIGMENT TYPE AND COLOR | (2) PIGMENT SOLIDS (WT. %) | (3) TYPE BINDER | (4) APPROX. $T_g$ BINDER (° C.) | (5) BINDER SOLIDS (WT. %) | (6) BINDER TO PIGMENT RATIO | (7) VEHICLE | (8) CONTAINS WAX | (9) CROSSLINKING AGENT | (10) CROSSLINKING AGENT AMOUNT (WT. %) |
|---|---|---|---|---|---|---|---|---|---|
| DIARYLIDE YELLOW 14 | 20.6 | POLYURETHANE DISPERSION | −30 | 10.0 | 0.5:1 | WATER | YES | NONE | — |

TABLE II-continued

PROPERTIES OF PREFERRED INK COMPOSITIONS

| (1) PIGMENT TYPE AND COLOR | (2) PIGMENT SOLIDS (WT. %) | (3) TYPE BINDER | (4) APPROX. $T_g$ BINDER (° C.) | (5) BINDER SOLIDS (WT. %) | (6) BINDER TO PIGMENT RATIO | (7) VEHICLE | (8) CONTAINS WAX | (9) CROSS-LINKING AGENT | (10) CROSS-LINKING AGENT AMOUNT (WT. %) |
|---|---|---|---|---|---|---|---|---|---|
| RUBINE MAGENTA RED 238 | 16.9 | POLYURETHANE DISPERSION | −30 | 10.7 | 0.7:1 | WATER | YES | NONE | — |
| PHTHALOCYAN BLUE 15:3 | 16.2 | POLYURETHANE DISPERSION | −30 | 10.0 | 0.6:1 | WATER | YES | NONE | — |
| RUBINE MAGENTA RED 238 | 15.2 | ETHYLENE VINYL ACETATE EMULSION | −15 | 18.2 | 1.2:1 | WATER | YES | NONE | — |
| PHTHALOCYAN BLUE 15:3 | 15.8 | ETHYLENE VINYL ACETATE EMULSION | −15 | 17.7 | 1.1:1 | WATER | YES | NONE | — |
| DIARYLIDE YELLOW 14 | 20.6 | ETHYLENE VINYL ACETATE EMULSION | +10 | 18.5 | 0.9:1 | WATER | YES | NONE | — |
| DIARYLIDE YELLOW 14 | 20.6 | ETHYLENE VINYL ACETATE EMULSION | +10 | 18.5 | 0.9:1 | WATER | YES | KYMENE PLUS | 6% |
| RUBINE MAGENTA RED 238 | 15.2 | ETHYLENE VINYL ACETATE EMULSION | +10 | 19.6 | 1.3:1 | WATER | YES | KYMENE PLUS | 6% |
| PHTHALOCYAN BLUE 15:3 | 15.8 | ETHYLENE VINYL ACETATE EMULSION | +10 | 19.0 | 1.2:1 | WATER | YES | KYMENE PLUS | 6% |
| CARBON BLACK 7 | 13.1 | ETHYLENE VINYL ACETATE EMULSION | +10 | 17.0 | 1.3:1 | WATER | YES | KYMENE PLUS | 6% |
| DIARYLIDE YELLOW 14 | 18.0 | STYRENE BUTADIENE LATEX EMULSION | −20 | 18.0 | 1.0:1 | WATER | YES | NONE | — |
| RUBINE MAGENTA RED 238 | 13.9 | STYRENE BUTADIENE LATEX EMULSION | −20 | 18.5 | 1.3:1 | WATER | YES | NONE | — |
| PHTHALOCYAN BLUE 13:3 | 13.0 | STYRENE BUTADIENE LATEX EMULSION | −20 | 17.5 | 1.3:1 | WATER | YES | NONE | — |
| CARBON BLACK 7 | 15.0 | STYRENE BUTADIENE LATEX EMULSION | −20 | 16.0 | 1.1:1 | WATER | YES | NONE | — |
| DIARYLIDE YELLOW 14 | 20.3 | ACRYLIC EMULSION POLYMER | −10 | 24.8 | 1.2:1 | WATER | YES | NONE | — |
| RUBINE MAGENTA RED 238 | 20.0 | ACRYLIC EMULSION POLYMER | −10 | 22.5 | 1.1:1 | WATER | YES | NONE | — |
| PHTHALOCYAN BLUE 15:3 | 20.2 | ACRYLIC EMULSION POLYMER | −10 | 24.5 | 1.2:1 | WATER | YES | NONE | — |
| CARBON BLACK 7 | 19.7 | ACRYLIC EMULSION POLYMER | −10 | 23.2 | 1.2:1 | WATER | YES | NONE | — |

In instances where the ink composition contains a binder having a $T_g$ above room temperature (i.e.; a $T_g$ of about 20° C. or more) it may be desirable to heat the ink composition to a temperature of about 10° C. above its glass transition temperature in order to facilitate formation of the ink film thereby enhancing adherence of the ink composition to the substrate.

In order to enhance adherence of the ink film to the paper, it is desirable that the ink films formed from the ink compositions of the present invention exhibit resistance to solubilization over a wide pH range. It is desirable that the ink films formed from the ink compositions of the present invention have a solubility as measured in either distilled deionized water or solventized alkaline solution of no more than about 85 milligrams of ink pigment per gram of dry ink film, preferably no more than about 20 milligrams of ink pigment per gram of dry ink film, more preferably no more than about 5 milligrams of ink pigment per gram of dry ink film, and even more preferably no more than about 0.5 milligrams of ink pigment per gram of dry ink film.

It is desirable that the ink films formed from the ink compositions of the present invention have an ink film toughness, as measured at 50% strain, of at least about 0.01 MPa and preferably of at least about 0.05 MPa. It is also desirable that these ink films be capable of withstanding a maximum strain of at least about 0.3 and preferably of at least about 1.

The mechanical properties of ink films prepared from the preferred ink compositions useful with the present invention are summarized in Table III. Referring to Table III, column 1 identifies the pigment type and color. Column 2 indicates the type of binder contained within the ink composition. Column 3 indicates the approximate $T_g$ of the binder. Column 4 indicates whether wax was added to the ink composition. Column 5 indicates whether a crosslinking agent was added to the ink composition. Column 6 indicates how much crosslinking agent was added to the ink composition based on weight. Column 7 indicates the ink film solubility in distilled deionized water. Column 8 indicates the ink film solubility in a solventized alkaline solution. The ink film solubilities indicated in column 7 and column 8 are recorded in milligrams of dissolved ink pigment per gram of dry ink film. Column 9 indicates the toughness of the ink films as measured at 50% strain. The toughness recorded for each ink composition in column 9 is based upon an average of three toughness measurements conducted on each ink composition. Column 10 indicates maximum strain of the ink film. The following procedure is used to generate the ink films upon which the solubility, toughness, and strain data are based.

Procedure A: Procedure for Generating Ink Films

In order to generate an ink film upon which solubility, toughness, and strain data are based, a sheet of polytetrafluoroethylene ("PTFE") is spread onto a flat surface such as a counter top. A PTFE (i.e.; TEFLON) sheet suitable for this purpose is model No. FP301300 commercially available from Goodfellow Corporation of Berwyn, Pa. and supplied in rolls which are 10 m in length, 0.1 mm thick, and 300 mm wide.

Using 1 cm wide tape strips, a rectangle 10 cm long×5 cm wide is circumscribed on the PTFE sheet. The tape should have a caliper between 0.4 mm and 0.5 mm. A suitable tape for this purpose is a 20 mil stickyback double liner tape commercially sold as FLEXMOUNT™ No. 412X18 STICKYBACK DL, available from 3M Corporation of St. Paul, Minn.

Using a liquid correction fluid such as BIC WITE-OUT, available from the BIC Corporation of Milford, Conn., any gaps between the tape strips should be filled in. After the liquid correction fluid is dry, the enclosed rectangle is filled with about 8.0 ml to 11.0 ml of the ink composition to be tested. The ink composition is allowed to cure at room temperature for two days so as to form an ink film. Those ink films made from ink compositions containing acrylic binders, are additionally cured by placing the film in an oven for one hour at 105° C.

Procedure B: Procedure For Making A Solventized Alkaline Solution

The following procedure is used to make a standard solventized alkaline solution used to generate the solubility data found in column 7 of Table III and the ΔE data found in column 10 of Tables VI–VIII and found in FIGS. 4–11.

To a beaker, add 0.40 grams of tetra sodium EDTA (i.e.; ethylene diamine tetra-acetic acid, tetra sodium salt hydrate powder of 98% purity), available from Aldrich Chemical Company of Milwaukee, Wis. To the tetra sodium EDTA, 0.20 grams of sodium carbonate powder of 99.5% purity is added. A sodium carbonate powder of 99.5% purity suitable for this purpose is available from Aldrich Chemical Company. To the sodium carbonate powder and the tetra sodium EDTA, 100 grams of distilled water is added. The mixture is stirred until the solids are completely dissolved.

To this solution, 1.70 grams of a $C_{12}$–$C_{14}$ alkyl dimethyl amine oxide nonionic surfactant is added. A suitable $C_{12}$–$C_{14}$ alkyl dimethyl amine oxide nonionic surfactant is BARLOX 12 sold as a 30% solution and available from Lonza Inc. of Fair Lawn, N.J. To this solution 9.50 grams of 2-butoxyethanol is added. A suitable 2-butoxyethanol is commercially available as a 99% solution from Union Carbide Corporation of Danbury, Conn. To this, 88 grams of distilled water is added. This solution is then stirred in order to provide mixing.

To this solution, 0.20 grams of a $C_9$–$C_{11}$ ethoxylated nonionic surfactant having an average of six ethoxylated groups per molecule is added. Prior to addition to the solution, the $C_9$–$C_{11}$ ethoxylated nonionic surfactant is heated in an oven at a temperature of about 75° C. to 100° C. for about 20 minutes until the surfactant is no longer cloudy. A suitable $C_9$–$C_{11}$ nonionic ethoxylated surfactant for this purpose is NEODOL 91-6 available as a 100% solution from Shell Oil Company of Houston, Tex.

The entire solution is stirred for about two minutes. The solution is then titrated with 12N sodium hydroxide until the pH is stable at 12.5. A suitable 12N sodium hydroxide is available from J.T. Baker a division of Mallinckrodt Incorporated of Phillipsburg, N.J. After it has been titrated to a stable pH of 12.5, the solution is then ready to be used as a standard solventized alkaline solution.

Immediately after preparation, the standard solventized alkaline solution is poured into a plastic container. In order to maintain the pH stability of the standard solution, the air space above the standard solution in the plastic container is then filled with gaseous nitrogen and the lid of the container tightly closed. Any air holes in the container are covered with tape while not in use. Before each use, the pH of the standard solution should be checked and adjusted to a pH of 12.5 if necessary.

Procedure C: Procedure for Measuring Solubility of the Ink Film

Referring to column 6 of Table III, the following procedure is used to measure the solubility of the ink films in distilled deionized water.

Using the same ink composition described above in Procedure A, a spectrophotometer is used to determine the maximum absorbance wavelength of each ink as well as the light absorption versus pigment concentration calibration lines of each ink composition.

For each of the preferred pigments of this invention, the maximum absorbance wavelength measured for each pigment color is as follows:

| | |
|---|---|
| Carbon Black 7 | 500 nanometers |
| Diarylide Yellow 14 | 430 nanometers |
| Rubine Magenta Red 238 | 580 nanometers |
| Phthalocyan Blue 15:3 | 610 nanometers |

To determine the solubility in distilled deionized water, three ink film samples, each 1 cm×1 cm, are cut from the ink films made according to procedure A. Wearing latex gloves or similar, the PTFE backing is peeled from each ink film. Each ink film sample to be tested is weighed and then added to a vial containing 10 ml of distilled deionized water. The vial is handshaken for one minute and the contents filtered through a 25 mm glass fiber filter having a pore size of 1 micrometer. A suitable glass fiber filter for this purpose is a Gelman No. 4523 Glass Fiber Acrodisc Syringe Filter available from VWR Scientific of Chicago, Ill.

A spectrophotometer is then used to measure the light absorbance of the ink film filtrate. According to Beer-Lambert's Law, absorbance of light in the linear region of the light spectrum is a function of the concentration of the medium into which light is absorbed. Transmittance of light through a medium may be correlated with the known chromophore medium's concentration at a determined wavelength.

Pigment concentration, measured in milligrams of ink film per ml of distilled deionized water, can be calculated from the light absorbance of the ink film filtrate by applying Beer-Lambert's Law to the following equation:

$$y_{(abs)} = mx_{(conc)} + b$$

wherein $y_{(abs)}$, represents the light absorbance of the ink film filtrate, m, represents the slope of the light absorbance calibration line of the ink composition, $x_{(conc)}$, represents the pigment concentration and b represents the y-axis intercept. From the measured pigment concentration and the weight of the dry ink film, the solubility of the ink film can be determined in milligrams of dissolved ink pigment per gram of dry ink film.

A suitable spectrophotometer for measuring the light absorbance of the ink compositions and the ink film filtrate is the Diode Array Spectrophotometer, model No. 8452A, manufactured by the Hewlett-Packard Company of Palo Alto, Calif.

To determine the solubility of the ink films in a solventized alkaline solution as recorded in column 7 of Table III, the same procedure as outlined above for determining solubility in distilled deionized water is followed except that the standard solventized alkaline solution made according to Procedure B above is substituted for distilled deionized water.

For each ink composition tested the solubility data are generated in triplicate and an average solubility based on these three observations is calculated. Hence, the solubility data in columns 6 and 7 are based on an average of three observations for each of the seventeen ink compositions listed in Table III.

Procedure D: Procedure for Measuring Toughness and Strain of the Ink Film:

Referring to columns 8 and 9 respectively of Table III, the following procedure is used to measure the toughness and the maximum strain of the ink films. As shown in Table III, column 8, the ink film toughness was measured at 50% strain. Ink films made according to procedure A above are used for measuring toughness and maximum strain.

Using a sharp knife such as an Exacto knife, a uniformly level area of the ink film is cut into three separate rectangular ink film samples wherein each sample is 3 cm in length and 4 mm in width. Special care is taken when cutting the ink films to ensure that the edges are smoothly cut so as to prevent formation of notches around the edges of the ink film.

The caliper of each ink film sample is measured. A suitable device for measuring caliper is the Thwing-Albert caliper tester model No. 89-100 available from Thwing-Albert Instrument Company of Philadelphia, Pa. For purposes of measuring the caliper of the ink films, the Thwing-Albert caliper tester should be set to a pressure of 95 grams per square inch using a presser foot having a 5 cm diameter.

A tensile tester is used to determine both the toughness of the ink film and the maximum strain of the ink film. The tensile tester should be set to a 1 cm gage length and a load cell of 100N. The tensile tester should then be set such that the ink film has an initial slack of 0.5 cm and a crosshead speed of 0.15 cm/second. A suitable tensile tester for measuring toughness and strain of the ink film is the Instron tensile tester, model No. 4502 available from the Instron Corporation of Canton, Mass.

Approximately 1 cm of each longitudinal end of the ink film sample to be tested is attached to a crosshead to provide a 1 cm gage length and a 4 mm width. The extension and load are recorded. The stress of the ink film sample, σ, is determined from the following equation:

$$\sigma = \text{load}/(\text{ink film sample caliper} \ast \text{ink film sample width})$$

The strain of the ink film sample, ε, is determined from the following equation:

$$\epsilon = [(\text{length of stretched ink film} - \text{length of ink film before stretching})/\text{length of ink film before stretching}]$$

Toughness of the ink film at 50% strain is calculated by integrating the area under the stress-strain curve over the interval from 0 strain to 0.5 strain. The maximum strain of the ink film is defined as the strain at which the film breaks (i.e.; at the point where rupture occurs and the stress becomes zero).

The toughness data and maximum strain data in columns 8 and 9 respectively are each based on an average of three observations for each of the seventeen ink compositions listed in Table III.

TABLE III

MECHANICAL PROPERTIES OF INK FILMS PREPARED FROM THE PREFERRED INK COMPOSITIONS

| (1) PIGMENT COLOR AND TYPE | (2) TYPE BINDER | (3) APPROX. $T_g$ OF BINDER (° C.) | (4) WAX | (5) CROSS-LINKING AGENT | (6) CROSS-LINKING AGENT AMOUNT (WT. %) | (7) AVERAGE (N = 3) INK FILM SOLUBILITY-DISTILLED DEIONIZED WATER (mg/g) | (8) AVERAGE (N = 3) INK FILM SOLUBILITY-SOLVENTIZED ALKALINE SOLUTION (mg/g) | (9) AVERAGE (N = 3) INK FILM TOUGHNESS MEASURED @ 50% STRAIN (MPa) | (10) AVERAGE (N = 3) INK FILM MAXIMUM STRAIN |
|---|---|---|---|---|---|---|---|---|---|
| DIARYLIDE YELLOW 14 | POLY-URETHANE DISPERSION | −30 | YES | NONE | — | 0.21 ± 0.06 | 0.1 ± 0.008 | 0.791 ± 0.027 | 0.33 ± 0.02 |
| RUBINE MAGENTA 238 | POLY-URETHANE DISPERSION | −38 | YES | NONE | — | 0.83 ± 0.01 | 0.03 ± 0.02 | 0.569 ± 0.856 | 0.92 ± 0.12 |
| PHTHALOCYAN BLUE 13:3 | POLY-URETHANE DISPERSION | −30 | YES | NONE | — | ND | ND | 0.435 ± 0.813 | 8.92 ± 0.10 |

TABLE III-continued

MECHANICAL PROPERTIES OF INK FILMS PREPARED FROM THE PREFERRED INK COMPOSITIONS

| (1) PIGMENT COLOR AND TYPE | (2) TYPE BINDER | (3) APPROX. $T_g$ OF BINDER (° C.) | (4) WAX | (5) CROSS-LINKING AGENT | (6) CROSS-LINKING AGENT AMOUNT (WT. %) | (7) AVERAGE (N = 3) INK FILM SOLUBILITY-DISTILLED DEIONIZED WATER (mg/g) | (8) AVERAGE (N = 3) INK FILM SOLUBILITY-SOLVENTIZED ALKALINE SOLUTION (mg/g) | (9) AVERAGE (N = 3) INK FILM TOUGNESS MEASURED @ 50% STRAIN (MPa) | (10) AVERAGE (N = 3) INK FILM MAXIMUM STRAIN |
|---|---|---|---|---|---|---|---|---|---|
| RUBINE MAGENTA RED 238 | ETHYLENE VINYL ACETATE EMULSION | −15 | YES | NONE | — | 0.10 ± 0.003 | ND | 0.110 ± 0.801 | 22.30 ± 1.15 |
| PHTHALOCYAN BLUE I5:3 | ETHYLENE VINYL ACETATE EMULSION | −15 | YES | NONE | — | ND | ND | 0.061 ± 8.802 | 28.60 ± 2.50 |
| DIARYLIDE YELLOW 14 | ETHYLENE VINYL ACETATE EMULSION | +10 | YES | KYMENE PLUS | 6% | ND | ND | 0.084 ± 8.006 | 14.68 ± 0.46 |
| RUBINE MAGENTA RED 238 | ETHYLENE VINYL ACETATE EMULSION | +10 | YES | KYMENE PLUS | 6% | ND | ND | 0.131 ± 0.003 | 14.28 ± 0.21 |
| PHTHALOCYAN BLUE 15:3 | ETHYLENE VINYL ACETATE EMULSION | +10 | YES | KYMENE PLUS | 6% | ND | ND | 0.084 ± 0.806 | 14.38 ± 0.44 |
| CARBON BLACK 7 | ETHYLENE VINYL ACETATE EMULSION | +10 | YES | KYMENE PLUS | 6% | 0.22 ± 0.12 | ND | 1.035 ± 0.828 | 1.80 ± 0.00 |
| DIARYLIDE YELLOW 14 | STYRENE BUTADTENE LATEX EMULSION | −28 | YES | NONE | — | ND | ND | 0.084 ± 0.00S | 4.2 ± 0.72 |
| RUBINE MAGENTA RED 238 | STYRENE BUTADTENE LATEX EMULSION | −28 | YES | NONE | — | 68 ± 40.8 | 17 ± 1.58 | 0.080 ± 0.006 | 4.4 ± 0.55 |
| PHTHALOCYAN BLUE 15:3 | STYRENE BUTADTENE LATEX EMULSION | −20 | YES | NONE | — | 0.23 ± 0.84 | 0.26 ± 0.12 | 0.070 ± 0.087 | 4.4 ± 0.55 |
| CARBON BLACK 7 | STYRENE BUTADTENE LATEX EMULSION | −20 | YES | NONE | — | 83 ± 32 | 24 ± 9.2 | 8.020 ± 0.806 | 1.4 ± 1.07 |
| DIARYLIDE YELLOW 14 | ACRYLIC EMULSION POLYMER | −10 | NO | NONE | — | 0.16 ± 0.807 | 0.16 ± 0.02 | 0.117 ± 0.10 | 28 ± 3.60 |
| RUBINE MAGENTA RED 238 | ACRYLIC EMULSION POLYMER | −18 | NO | NONE | — | 0.06 ± 0.084 | 0.0S ± 0.01 | 0.105 ± 8.007 | 28 ± 3.68 |
| PHTHALOCYAN BLUE 15:3 | ACRYLIC EMULSION POLYMER | −10 | NO | NONE | — | 0.05 ± 0.083 | 0. ± 0.84 | 0.147 ± 0.005 | 28 ± 3.68 |
| CARBON BLACK 7 | ACRYLIC EMULSION POLYMER | −10 | NO | NONE | — | 0.07 ± 0.8586 | 0.10 ± 0.82 | 0.240 ± 0.056 | 20 ± 3.68 |

ND — Below the detection limit
NA — Not available

Inks suitable for the present invention are commercially available from Sun Chemical Corporation of Northlake, Ill. A list of these inks is provided in Table IV.

TABLE IV

| (1) PRODUCT NAME | (2) TYPE | (3) PIGMENT COLOR | (4) VEHICLE | (5) TYPE BINDER | (6) APPROX. $T_g$ OF BINDER | (7) CONTAINS WAX |
|---|---|---|---|---|---|---|
| SUN CHEMICAL WKF20712F | FINISHED INK | DIARYLIDE YELLOW 14 | WATER | POLYURETHANE DISPERSION | −30 | YES |
| SUN CHEMICAL WKF41508F | FINISHED INK | RUBINE MAGENTA RED 238 | WATER | POLYERETNANE DISPERSION | −30 | YES |
| SUN CHEMICAL WKF51310F | FINISHED INK | PHTHALOCYAN BLUE 15:3 | WATER | POLYURETHANE DISPERSION | −30 | YES |
| SUN CHEMICAL WKG41584F | FINISHED INK | RUBINE MAGENTA RED 238 | WATER | ETHYLENE VINYL ACETATE EMULSION | −15 | YES |
| SUN CHEMICAL WKG51372F | FINISHED INK | PHTHALOCYAN BLUE 15:3 | WATER | ETHYLENE VINYL ACETATE EMULSION | −15 | YES |
| SUN CHEMICAL WKG20762F | FINISHED INK | DIARYLIDE YELLOW 14 | WATER | ETHYLENE VINYL ACETATE EMULSION | +10 | YES |
| SUN CHEMICAL WKG41585P | FINISHED INK | RUBINE MAGENTA RED 238 | WATER | ETHYLENE VINYL ACETATE EMULSION | +10 | YES |
| SUN CHEMICAL WKG51373F | FINISHED INK | PHTHALOCYAN BLUE 15:3 | WATER | ETHYLENE VINYL ACETATE EMULSION | +10 | YES |
| SUN CHEMICAL WKG90603F | FINISHED INK | CARBON BLACK 7 | WATER | ETHYLENE VINYL ACETATE EMULSION | +10 | YES |
| SUN CHEMICAL WKHFW283-0204 | FINISHED INK | DIARYLIDE YELLOW 14 | WATER | STYRENE BUTADIENE LATEX EMULSION | −20 | YES |
| SUN CHEMICAL WKHFW483-0203 | FINISHED INK | RUBINE MAGENTA RED 238 | WATER | STYRENE BUTADIENE LATEX EMULSION | −20 | YES |
| SUN CHEMICAL WKHFW583-0205 | FINISHED INK | PHTHALOCYAN BLUE 15:3 | WATER | STYRENE BUTADIENE LATEX EMULSION | −20 | YES |
| SUN CHEMICAL WKHFW983-0206 | FINISHED INK | CARBON BLACK 7 | WATER | STYRENE BUTADIENE LATEX EMULSION | −20 | YES |
| SUN CHEMICAL *YPD-9773 | PIGMENT DISPERSION | DIARYLIDE YELLOW 14 | WATER | NONE | — | NO |
| SUN CHEMICAL *RPD-9775 | PIGMENT DISPERSION | RUBINE MAGENTA RED 238 | WATER | NONE | — | NO |
| SUN CHEMICAL *BPD-9777 | PIGMENT DISPERSION | PHTHALOCYAN BLUE 15:3 | WATER | NONE | — | NO |
| SUN CHEMICAL *LPD-9776 | PIGMENT DISPERSION | CARBON BLACK 7 | WATER | NONE | — | NO |

*Note: Pigment Dispersion comprised of pigment solids, surfactant, and water.

Ink may be applied to the fibrous sheet in any number ways including but not limited to: dipping the fibrous sheet into a solution of ink, spraying a solution of ink onto the fibrous sheet, or preferably by printing the ink onto the fibrous sheet. Printing processes suitable for this invention include but are not limited to: lithography, letterpress, ink jet printing, gravure, screen printing, intaglio and preferably flexography. A single color image or multi-color image may be applied to the fibrous sheet. Devices suitable for applying an image onto a sanitary disposable paper product utilizing the ink and fibrous sheet of this invention are described in commonly assigned U.S. Pat. No. 5,213,037 issued to Leopardi, II on May 25, 1993 and U.S. Pat. No. 5,255,603 issued to Sonneville et al. issued on Oct. 26, 1993, the disclosures of which are incorporated herein by reference.

The printed image produced on the paper can be line work, halftoning, preferably a process print, or a combination of these. As used herein, "line work" refers to a printed image composed of solids and lines. As used herein, "process print" refers to a halftone color print created by the color separation process whereby an image composed of two or more transparent inks is broken down into halftone dots which can be recombined to produce the complete range of colors of the original image.

Coloration in a process print image is produced by varying the area of ink deposition in a given image area frequency of ink deposition and the number of inks in the image area. Ink deposition area may be varied by adjusting the frequency, size, or combination thereof of halftone dots. As used herein, "transparent ink" or "process ink" refers to an ink which has minimal hiding power thus allowing some of the light to pass through it. With a transparent ink, light must be able to penetrate one or more ink layers while only certain wavelengths are absorbed. To make a red, for example, yellow is printed over magenta. Yellow absorbs blue wavelengths allowing red and green wavelengths to pass through. Magenta absorbs green wavelengths. The remaining wavelengths are reflected as red.

In contrast to transparent inks, when opaque inks (i.e.; non-transparent inks) are overlayed, the top color is the dominant color since it absorbs most light other than the specific wavelengths of its color. For example, an opaque yellow ink would absorb blue wavelengths while reflecting the red and green wavelengths to produce a yellow.

An image is process printed, if the image is printed with multiple process colors. The process colors must have a linescreen or dot size. Furthermore, the inks must be transparent to produce a multitude of colors when the inks are overlayed.

The advantage of a process printed image over a line work printed image is that the process printed image enables many colors and shades of those colors to be produced with a few inks. For example, a human image may be comprised of ten or more colors. This image can be reproduced by process printing utilizing as few as three colors. The same image reproduced by line work would typically require ten or more inks each with a corresponding printing station on the printing press. A printed image produced by line work often increases both the cost and the complexity of reproducing the image. Though the preferred ink compositions of the present invention are pigment-based process inks, other types of pigment-based inks are within the scope of this invention.

The color density of an image may be measured with a densitometer. Color density, a dimensionless measurement, refers to the density of the color produced by the ink. The higher the color density of the ink, the greater the intensity or strength of the color. As color density increases, the densitometer measurements also increase. The densitometer measures the color density of the dominant primary color present in the image. The densitometer then displays the color density of the dominant primary color. As used herein, "primary color" refers to one of the four colors of yellow, cyan, magenta, and black.

Procedure E: Procedure for Measuring Color Density of a Printed Image

The color density of an image printed on a sanitary disposable paper product may be measured as follows: Using a reflectance densitometer, the densitometer setting is adjusted so as to read the dominant primary color present in the image. The printed sanitary disposable paper product sample is placed on top of four unprinted sheets. The four unprinted sheets are used in order to eliminate the influence of background color from a colored surface.

These four sheets of a white substrate having an $L^*a^*b^*$ value, of about 91.17, 0.64, and 4.29, respectively may be used wherein the $L^*a^*b^*$ value is measured by a spectrocolorimeter set to a 10° observer angle with illuminant A in the CIELAB $L^*a^*b^*$ mode. A white substrate having an $L^*a^*b^*$ value of about 91.17, 0.64, and 4.29 respectively is white BOUNTY® paper towel marketed by the instant assignee.

Three color density measurements are made within a given color of an image using the reflectance densitometer. The average of the three measurements is calculated and recorded.

Color density measurements may be measured on any ink that is applied to any color substrate. Preferably color density is measured on any substrate with a white background having an $L^*a^*b^*$ of about 91.17, 0.64, and 4.29, respectively. A suitable densitometer for measuring color density is the X-RITE 418 reflectance densitometer commercially available from X-Rite, Inc. of Grandville, Mich.

As used herein, "$L^*a^*b^*$", refers to the CIELAB $L^*a^*b^*$ color definition system. The CIELAB $L^*a^*b^*$ color definition system evaluates the color variation in a defined area of a sample and compares this variation to that of a standard reference. The colors are defined by a set of mathematical functions known as $L^*a^*b^*$ values, which describe the human eye's sensitivity to color. The $L^*$ relates to the lightness of the sample. The $a^*$ refers to the redness of the sample if the value of $a^*$ is positive. If the value of $a^*$ is negative, it refers to the greenness of the sample. The $b^*$ refers to the yellowness of the sample if the value of $b^*$ is positive. If the value of $b^*$ is negative, it refers to the blueness of the sample. From the $L^*a^*b^*$ values a $\Delta E$ value, a dimensionless measurement, can be determined wherein $\Delta E$ represents the difference in color between two different sets of $L^*a^*b^*$ values. The greater the $\Delta E$, the greater the color difference.

Procedure F: Procedure for Generating Ink Rub-off

The method used to evaluate the rub-off resistance of an ink composition after it has been applied to a substrate simulates scrubbing a countertop with the applied pressure of one finger. The method comprises rubbing a known area of a printed substrate against a white tile having a known surface profile. Rubbing is performed at a predetermined pressure, speed, and stroke length, for a fixed number of strokes. Colorimetry can then be used to quantify the ink transferred from the printed paper to the tile.

A white tile 10.15 cm in length by 10.15 cm in width and 0.6 cm in thickness is used for this purpose. The white tile is constructed of a white surface, 0.11 cm in thickness which is adhesively laminated to a tempered hardboard support base which is 0.5 cm in thickness. A typical white surface used for this purpose has a CIELAB $L^*a^*b^*$ value of about 93.65, −0.32, and 0.11 respectively; a kinetic coefficient of friction of about 0.14 as measured against an aluminum surface with an applied pressure of 47 grams per square inch; and a surface roughness of about 3.53 micrometers as measured via interferometry. An instrument useful for measuring surface roughness via interferometry is a Zygo New View 200, model No. 97-51-60655, manufactured by Zygo Corporation of Middlefield, Conn. A white surface suitable for this purpose is white FORMICA No. 459 available from Formica Corporation of Cincinnati, Ohio. A suitable tempered hardboard support base is available from Georgia-Pacific Corporation of Atlanta, Ga. A suitable adhesive useful for laminating the white surface to the base is Model No. 30NF available from 3M Corporation of St. Paul, Minn.

Figures 2, 2A:
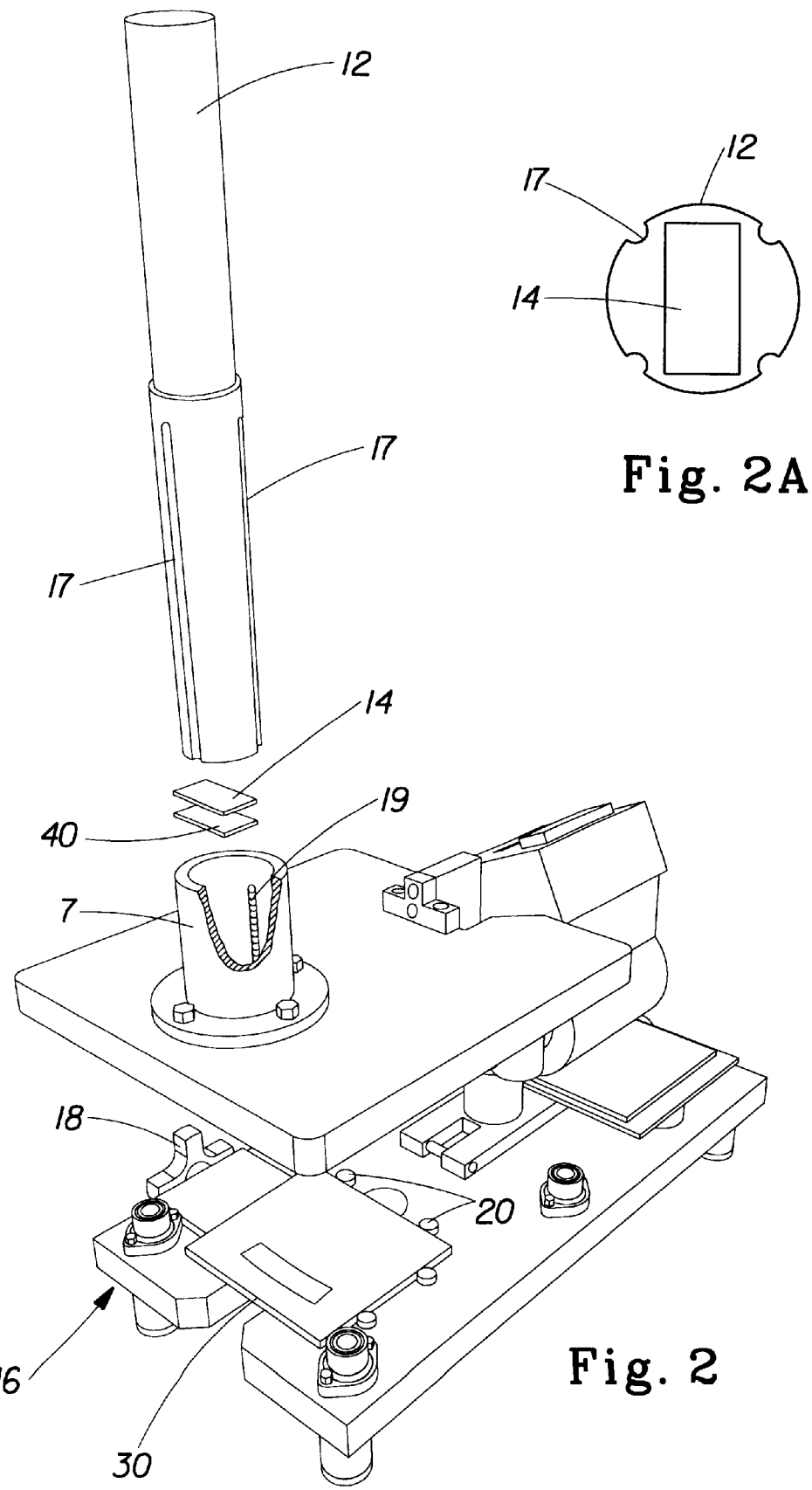
FIG. 2 is a rear exploded perspective view of the ink rub tester of FIG. 1.
FIG. 2A is a bottom view of the metal spline, the spline indentations and the rubber foot of FIG. 1.
Figure 3:
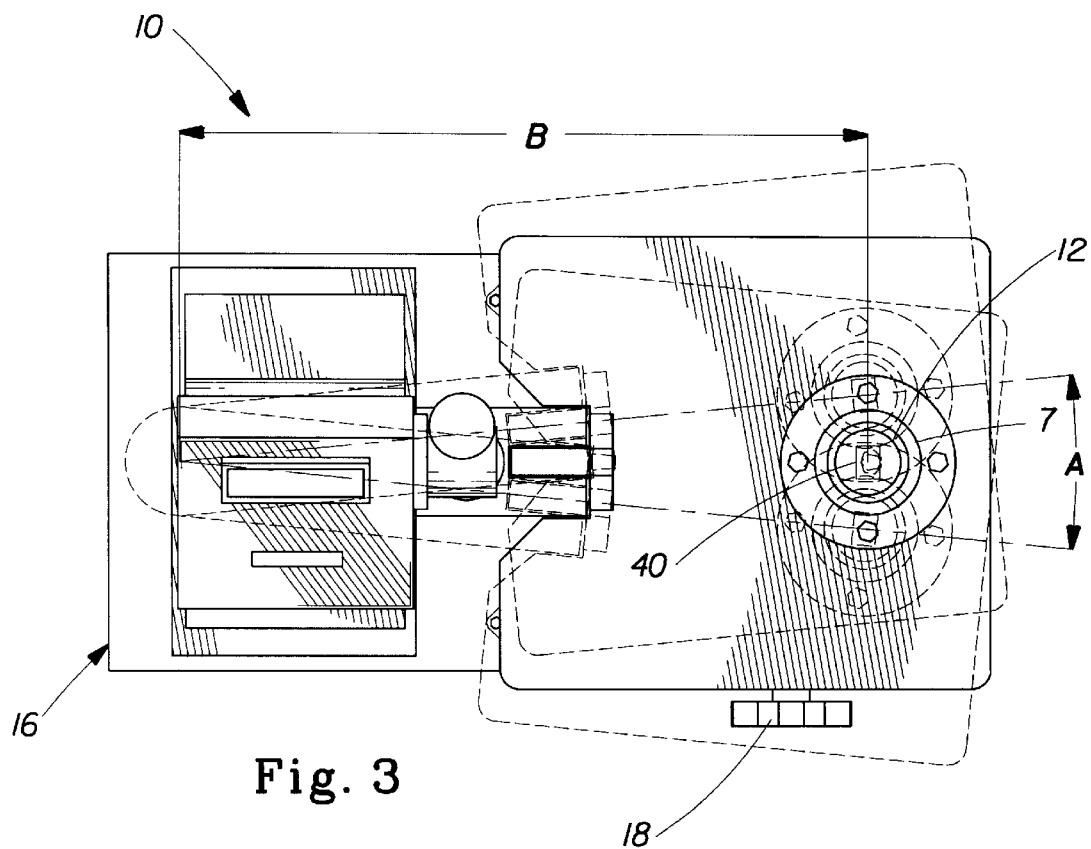
FIG. 3 is a top plan view of the ink rub tester of FIG. 1.

An ink rub tester 10 may be used to simulate scrubbing a countertop such as that shown in FIGS. 1–3. Referring to FIGS. 2 and 2A, a rubber foot 14 which is 1.2 cm in length by 0.9 cm in width is attached to the bottom of a 1000 gram metal spline 12. The rubber foot 14 is oriented on the metal spline 12 such that the lengthwise dimension of the rubber foot 14 is parallel to the spline ribs 19 and the spline indentations 17.

The rubber foot 14 is made of off-white neoprene rubber having a thickness of 0.125 inch; a tensile strength of 1200 psi, and a Shore A durometer hardness of 55. A suitable neoprene rubber material for this purpose is sold as item No. 8616K64 available from McMaster-Carr Supply Company of Chicago, Ill. The rubber foot 14 is adhesively attached to the metal spline 12. A preferred adhesive for this purpose is DURO QUICK GEL NO-RUN SUPER GLUE manufactured by Loctite Corporation of Hartford, Conn.

A 1.2 cm by 0.9 cm single ply of the paper sample 40 to be evaluated is provided. The paper sample 40 should be of uniform color and color density. If a uniform paper sample 40 is not available, several paper samples of uniform color densities may be pieced together to provide one uniform 1.2 cm by 0.9 cm paper sample 40. Using a double-sided stickyback nonporous tape which has adhesive applied to both sides of the nonporous tape, the paper sample 40 to be evaluated is attached to the stickyback nonporous tape. The stickyback nonporous tape is then attached to the rubber foot 14 such that the paper sample 40 is in alignment with the rubber foot 14. A suitable stickyback nonporous tape for this purpose is a 20 mil stickyback double liner tape commercially sold as FLEXMOUNT™ No. 412X18 STICKY-BACK DL, available from 3M Corporation of St. Paul, Minn.

The white tile 30 is placed into the base 16 of the ink rub tester 10 and held securely in place. The white tile 30 may be held securely in place by tightening the tile holder adjustment screw 18 until the tile holder adjustment screw 18 engages the white tile 30 and holds it securely in place against the side pins 20. The white tile 30 should be flush with the base 16.

Referring to FIG. 2, a liquid to be tested is applied to the white tile 30. For this purpose a 25 microliter sample of the desired liquid is placed on the white tile 30. The liquid is placed on the white tile 30 such that the liquid will be directly aligned with the paper sample 40 attached to the rubber foot 14 of the metal spline 12 upon lowering the metal spline 12 into the spline holder 7. The metal spline 12 is lowered into the spline holder 7 such that the rubber foot 14 of the metal spline 12 contacts the liquid on the white tile 30. The metal spline 12 must be carefully lowered so as not to cause the liquid on the white tile 30 to splatter. Splattering changes the amount of liquid that the paper sample 40 contacts and thus impacts the rub-off results.

Figure 3A:
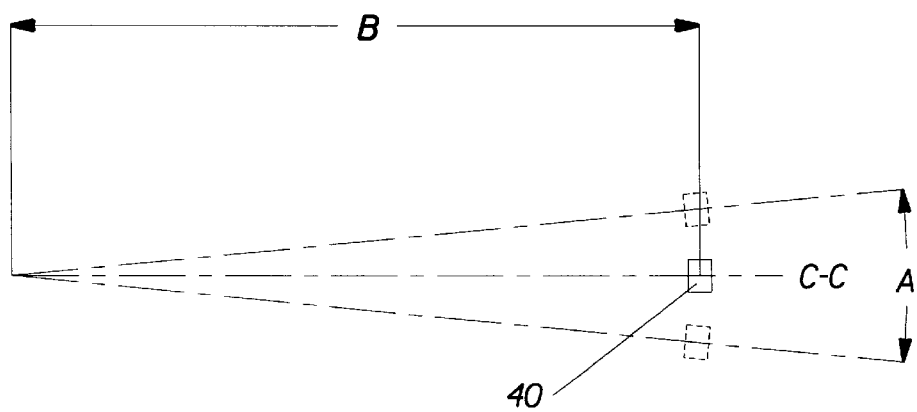
FIG. 3A is a top plan view of the paper sample of FIG. 3 during one complete cycle.

Upon contact with the white tile 30, the metal spline 12 exerts a constant force upon the white tile 30 of 9.81 N. Referring to FIG. 3, the paper sample 40 attached to the rubber foot 14 of the metal spline 12 is then rubbed against the surface of the white tile 30 for 7 cycles at a speed of 44.28 cycles/minute over a swept angle of 11.2 degrees (represented in FIG. 3 by "A") with a radius of 29.2 cm (represented in FIG. 3 by "B"). Referring to FIG. 3A, the paper sample 40 is positioned at the bisector of the swept angle (represented by line "C—C" in FIG. 3A) at both the beginning and the end of the 7 cycles. The orientation of the paper sample 40 with respect to the metal spline 12 and the spline holder 7 does not change throughout the test. The length of the paper sample 40 remains parallel to the tangent of the arc formed by the swept angle "A" and the radius "B" as shown in FIG. 3A.

A preferred ink rub tester 10 for test purposes is the CRC 1280 Ink Rub Tester, available from the Concord-Renn Company of Cincinnati, Ohio.

In order to obtain an accurate measure of rub-off, five observations on a given color for a given paper substrate are generated and averaged.

Procedure G: Procedure for Measuring Ink Rub-off Resistance

After the white tile 30 is allowed to dry for twenty-four hours the amount of ink rubbed off the paper substrate and transferred to the white tile 30 is evaluated by measuring the difference in color of the white tile 30 prior to rubbing and after rubbing according to the CIELAB L*a*b* color definition system.

In regards to the present invention, ΔE, is the difference in L*a*b* values between the white tile 30 prior to rubbing and the same white tile 30 after the white tile 30 has been rubbed against the surface of the substrate to which the ink is applied. The value of ΔE is defined by the following equation:

$$\Delta E = \sqrt{(L^*_1 - L^*_0)^2 + (a^*_1 - a^*_0)^2 + (b^*_1 - b^*_0)^2}$$

wherein $L^*_0$, $a^*_0$, and $b^*_0$ refer to the L*a*b* value of the white tile 30 prior to rubbing and $L^*_1$, $a^*_1$, and $b^*_1$ refer to the L*a*b* value of the white tile 30 after rubbing. The higher the value of ΔE of the white tile 30 after rubbing, the greater the amount of ink deposited on the surface of the white tile 30.

A spectrocolorimeter can be used to determine ΔE. For purposes of this invention, prior to making any measurements, the spectrocolorimeter is set to a 10° observer angle with illuminant A and is also set so as to measure in the CIELAB L*a*b* mode. As the measured L*a*b* value of the white tile 30 prior to rubbing may vary from white tile 30 to white tile 30, a standard L*a*b* reference value for the white tile 30 may be entered into the spectrocolorimeter. A typical standard L*a*b* reference value for a white tile 30 such as that described in Procedure F, is 93.65, −0.32, and 0.11, respectively. Each white tile 30 is checked against this reference value prior to rubbing. If the ΔE value between the white tile 30 prior to rubbing and the reference value is greater than 0.40, a new reference value is entered into the spectrocolorimeter based on the L*a*b* value of the white tile 30 before rubbing.

After the white tile 30 has been checked against the reference value and a new reference value entered if necessary, the spectrocolorimeter is used to measure the L*a*b* value and ΔE value of the rub. Eight equally spaced measurements are made with the spectrocolorimeter down the center of the rub. The spectrocolorimeter calculates an L*a*b* value and a ΔE value for each measurement. The spectrocolorimeter also calculates an average ΔE value of the rub based on the eight measurements. The spectrocolorimeter should be capable of reading a circular area between 5 mm to 7 mm in diameter. A suitable spectrocolorimeter for use with this invention is the X-RITE 948 commercially available from X-Rite, Inc. of Grandville, Mich.

Referring to Tables V–VIII, the ink rub-off resistance is shown for paper towel substrates printed at different color densities utilizing the ink compositions of the present invention. White BOUNTY® paper towel manufactured by the instant assignee was used for this purpose. All the inks represented in Tables V–VIII are process inks. The four tables are divided by ink pigment color. Table V represents BOUNTY® paper towel substrates printed with process inks utilizing Carbon Black 7 pigment. Table VI represents BOUNTY® paper towel substrates printed with process inks utilizing Phthalocyan Blue 15:3 pigment. Table VII represents BOUNTY® paper towel substrates printed with process inks utilizing Rubine Magenta Red 238 pigment. Table VIII represents BOUNTY® papertowel substrates printed with process inks utilizing Diarylide Yellow 14 pigment.

Referring to Tables V–VIII, Column 1 indicates the type of pigment used in the ink composition. Column 2 indicates the type of binder used in the ink composition. Column 3 indicates the approximate $T_g$ of the binder. Column 4 indicates the crosslinking agent, if any, added to the ink composition. Column 5 indicates the amount of crosslinking agent, if any, added to the ink composition.

Column 6 indicates whether wax was added to the ink composition. Column 7 indicates whether the substrate was heated to 135° C. after application of the ink to the substrate. Column 8 indicates the dominant primary color of the image printed on the paper towel substrate as indicated by the reflectance densitometer and measured according to Procedure E above. Column 9 indicates the color density of the image printed on the paper towel substrate as measured by the reflectance densitometer according to Procedure E above.

Column 10 indicates the rub-off resistance for each ink composition as applied to white BOUNTY® paper towel substrate and determined according to Procedures F and G above. Sigma ΔE (i.e.; ΣΔE) represents the summation of the ΔE of the ink composition in distilled water and the summation of the ΔE of the ink composition in a solventized alkaline solution wherein the solventized alkaline solution was made according to Procedure B above.

TABLE V

RUB-OFF RESISTANCE OF PAPER TOWEL SUBSTRATES PRINTED WITH BLACK INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| CARBON BLACK 7 | STYRENE BUTADIENE LATEX EMULSION | −20 | NONE | — | YES | NO | BLACK | 0.51 | 1.58 |
| CARBON BLACK 7 | STYRENE BUTADIENE LATEX EMULSION | −20 | NONE | — | YES | NO | BLACK | 0.65 | 1.62 |
| CARBON BLACK 7 | STYRENE BUTADIENE LATEX EMULSION | −20 | NONE | — | YES | NO | BLACK | 1.01 | 2.70 |
| CARBON BLACK 7 | STYRENE BUTADIENE LATEX EMULSION | −20 | NONE | — | YES | NO | BLACK | 0.83 | 2.90 |
| CARBON BLACK 7 | ACRYLIC EMULSION POLYMER | −10 | NONE | — | NO | YES | BLACK | 0.86 | 3.27 |
| CARBON BLACK 7 | ETHYLENE VINYL ACETATE EMULSION | +10 | KYMENE PLUS | 6% | YES | NO | BLACK | 0.52 | 8.22 |
| CARBON BLACK 7 | ETHYLENE VINYL ACETATE EMULSION | +10 | KYMENE PLUS | 6% | YES | NO | BLACK | 0.81 | 9.50 |
| CARBON BLACK 7 | ETHYLENE VINYL ACETATE EMULSION | +10 | NONE | — | YES | YES | BLACK | 0.95 | 10.15 |
| CARBON BLACK 7 | ACRYLIC EMULSION POLYMER | −10 | NONE | — | NO | YES | BLACK | 0.99 | 10.98 |
| CARBON BLACK 7 | ETHYLENE VINYL ACETATE EMULSION | +10 | KYMENE PLUS | 6% | YES | NO | BLACK | 0.96 | 12.13 |
| CARBON BLACK 7 | ETHYLENE VINYL ACETATE EMULSION | +10 | KYMENE PLUS | 6% | YES | NO | BLACK | 0.69 | 12.16 |
| CARBON BLACK 7 | STYRENE BUTADIENE LATEX EMULSION | −20 | NONE | — | YES | NO | BLACK | 1.41 | 13.21 |

TABLE VI

RUB-OFF RESISTANCE OF PAPER TOWEL SUBSTRATES PRINTED WITH CYAN INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT (WT. %) | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| PHTHALO-CYAN BLUE 15:3 | STYRENE BUTADIENE LATEX EMULSION | −20 | NONE | — | YES | NO | CYAN | 0.86 | 3.58 |
| PHTHALO-CYAN BLUE 15:3 | STYRENE BUTADIENE LATEX EMULSION | −20 | NONE | — | YES | NO | CYAN | 1.00 | 3.67 |
| PHTHALO-CYAN BLUE 15;3 | STYRENE BUTADIENE LATEX EMULSION | −20 | NONE | — | YES | NO | CYAN | 0.66 | 4.39 |
| PHTHALO-CYAN BLUE 15:3 | ETHYLENE VINYL ACETATE EMULSION | −15 | NONE | — | YES | YES | CYAN | 1.01 | 7.26 |
| PHTHALC-CYAN BLUE 15:3 | ETHYLENE VINYL ACETATE EMULSION | −15 | NONE | — | YES | NO | CYAN | 1.03 | 8.07 |
| PHTHALO-CYAN BLUE 15:3 | STYRENE BUTADIENE LATEX EMULSION | −20 | NONE | — | YES | NO | CYAN | 1.21 | 8.14 |
| PHTHALO-CYAN BLUE 15:3 | ACRYLIC EMULSION POLYMER | −10 | NONE | — | NO | YES | CYAN | 0.85 | 5.77 |
| PHTHALO-CYAN BLUE 15:3 | ETHYLENE VINYL ACETATE EMULSION | −15 | NONE | — | YES | NO | CYAN | 0.67 | 11.05 |
| PHTHALC-CYAN BLUE 15:3 | ETHYLENE VINYL ACETATE EMULSION | −15 | NONE | — | YES | NO | CYAN | 1.12 | 11.88 |
| PHTHALO-CYAN BLUE JS:3 | POLYURETHANE DISPERSION | −30 | NONE | — | YES | NO | CYAN | 0.64 | 11.99 |
| PHTHALO-CYAN BLUE 15:3 | ETHYLENE VINYL ACETATE EMULSION | −15 | NONE | — | YES | NO | CYAN | 0.87 | 12.23 |
| PHTHALO-CYAN BLUE 15:3 | POLYURETHANE DISPERSION | −30 | NONE | — | YES | NO | CYAN | 1.00 | 13.10 |
| PHTHALO-CYAN BLUE 15:5 | POLYURETHANE DISPERSION | −30 | NONE | — | YES | NO | CYAN | 0.49 | 13.38 |
| PHTHALO-CYAN BLUE 15:3 | STYRENE BUTADIENE LATEX EMULSION | −20 | NONE | — | YES | NO | CYAN | 1.41 | 15.20 |
| PHTHALO-CYAN BLUE 15:3 | POLYURETHANE DISPERSION | −30 | NONE | — | YES | NO | CYAN | 1.13 | 15.39 |

TABLE VI-continued

RUB-OFF RESISTANCE OF PAPER TOWEL SUBSTRATES PRINTED WITH
CYAN INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT (WT. %) | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| PHTHALO-CYAN BLUE 15:3 | POLYURETHANE DISPERSION | −30 | NONE | — | YES | NO | CYAN | 9.85 | 15.52 |
| PHTHALO-CYAN BLUE 15:3 | ETHYLENE VINYL ACETATE EMULSION | −10 | KYMENE PLUS | 6% | YES | NO | CYAN | 0.55 | 21.71 |
| PHTHALO-CYAN BLUE 15:3 | ETHYLENE VINYL ACETATE EMULSION | −15 | NONE | — | YES | NO | CYAN | 0.51 | 22.05 |
| PHTHALO-CYAN BLUE 15:3 | ETHYLENE VINYL ACETATE EMULSION | +10 | KYMENE PLUS | 6% | YES | NO | CYAN | 0.66 | 26.47 |
| PHTHALO-CYAN BLUE 15:3 | ETHYLENE VINYL ACETATE EMULSION | +10 | KYMENE PLUS | 6% | YES | NO | CYAN | 1.00 | 28.52 |
| PHTHALO-CYAN BLUE 15:3 | ACRYLIC EMULSION POLYMER | −10 | NONE | — | NO | YES | CYAN | 0.98 | 29.83 |
| PHTHALO-CYAN BLUE 15:3 | ETHYLENE VINYL ACETATE EMULSION | +10 | KYMENE PLUS | 6% | YES | NO | CYAN | 0.87 | 30.62 |

TABLE VII

RUB-OFF RESISTANCE OF PAPER TOWEL SUBSTRATES PRINTED WITH
MAGENTA INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| RUBINE MAGENTA RED 238 | STYRENE BUTADIENE LATEX EMULSION | −20 | NONE | — | YES | NO | MAGENTA | 0.52 | 2.51 |
| RUBINE MAGENTA RED 238 | ETHYLENE VINYL ACETATE EMULSION | −15 | NONE | — | YES | YES | MAGENTA | 0.96 | 4.27 |
| RUBINE MAGENTA RED 238 | ETHYLENE VINYL ACETATE EMULSION | −15 | NONE | — | YES | NO | MAGENTA | 6.53 | 4.70 |
| RUBINE MAGENTA RED 238 | ETHYLENE VINYL ACETATE EMULSION | −15 | NONE | — | YES | NO | MAGENTA | 0.96 | 5.36 |
| RUBINE MAGENTA RED 238 | ETHYLENE VINYL ACETATE EMULSION | −15 | NONE | — | YES | NO | MAGENTA | 0.84 | 5.87 |
| RUBINE MAGENTA RED 238 | ETHYLENE VINYL ACETATE EMULSION | −15 | NONE | — | YES | NO | MAGENTA | 0.66 | 6.03 |
| RUBINE MAGENTA RED 238 | ACRYLIC EMULSION POLYMER | −10 | NONE | — | NO | YES | MAGENTA | 0.84 | 7.13 |
| RUBINE MAGENTA RED 238 | POLYURETHANE DISPERSION | −30 | NONE | — | YES | NO | MAGENTA | 0.50 | 7.37 |
| RUBINE MAGENTA RED 238 | STYRENE BUTADIENE LATEX EMULSION | −20 | NONE | — | YES | NO | MAGENTA | 0.65 | 9.06 |
| RUBINE MAGENTA RED 238 | POLYURETHANE DISPERSION | −30 | NONE | — | YES | NO | MAGENTA | 0.63 | 9.07 |
| RUBINE MAGENTA RED 238 | POLYURETHANE DISPERSION | −30 | NONE | — | YES | NO | MAGENTA | 0.85 | 9.47 |
| RUBINE MAGENTA RED 238 | POLYURETHANE DISPERSION | −30 | NONE | — | YES | NO | MAGENTA | 1.03 | 10.22 |
| RUBINE MAGENTA RED 238 | ACRYLIC EMULSION POLYMER | −10 | NONE | — | NO | YES | MAGENTA | 1.00 | 12.39 |
| RUBINE | STYRENE BUTADIENE LATEX | −20 | NONE | — | YES | NO | MAGENTA | 0.84 | 14.66 |

TABLE VII-continued

RUB-OFF RESISTANCE OF PAPER TOWEL SUBSTRATES PRINTED WITH
MAGENTA INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| MAGENTA RED 238 | EMULSION | | | | | | | | |
| RUBINE MAGENTA RED 238 | ETHYLENE VINYL ACETATE EMULSION | +10 | KYMENE PLUS | 6% | YES | NO | MAGENTA | 0.54 | 14.73 |
| RUBINE MAGENTA RED 238 | ETHYLENE VINYL ACETATE EMULSION | +10 | KYMENE PLUS | 6% | YES | NO | MAGENTA | 0.96 | 13.63 |
| RUBINE MAGENTA RED 238 | ETHYLENE VINYL ACETATE EMULSION | +10 | KYMENE PLUS | 6% | YES | NO | MAGENTA | 0.67 | 15.78 |
| RUBINE MAGENTA RED 238 | ETHYLENE VINYL ACETATE EMULSION | +10 | KYMENE PLUS | 6% | YES | NO | MAGENTA | 0.86 | 16.91 |
| RUBINE MAGENTA RED 238 | STYRENE BUTADIENE LATEX EMULSION | −20 | NONE | — | YES | NO | MAGENTA | 1.20 | 18.53 |
| RUBINE MAGENTA RED 238 | POLYURETHANE DISPERSION | −30 | NONE | — | YES | NO | MAGENTA | 1.20 | 20.49 |
| RUBINE MAGENTA RED 238 | ETHYLENE VINYL ACETATE EMULSION | −15 | NONE | — | YES | NO | MAGENTA | 1.22 | 21.99 |
| RUBINE MAGENTA RED 238 | ETHYLENE VINYL ACETATE EMULSION | −15 | NONE | — | YES | NO | MAGENTA | 1.39 | 29.99 |
| RUBINE MAGENTA RED 238 | POLYURETHANE DISPERSION | −30 | NONE | — | YES | NO | MAGENTA | 1.38 | 31.03 |
| RUBINE MAGENTA RED 238 | STYRENE BUTADIENE LATEX EMULSION | −20 | NONE | — | YES | NO | MAGENTA | 1.41 | 34.39 |

TABLE VIII

RUB-OFF RESISTANCE OF PAPER TOWEL SUBSTRATES PRINTED WITH
YELLOW INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| DIARYLIDE YELLOW 14 | STYRENE BUTADIENE LATEX EMULSION | −20 | NONE | — | YES | NO | YELLOW | 0.84 | 5.10 |
| DIARYLIDE YELLOW 14 | STYRENE BUTADIENE LATEX EMULSION | −20 | NONE | — | YES | NO | YELLOW | 0.66 | 5.75 |
| DIARYLIDE YELLOW 14 | STYRENE BUTADIENE LATEX EMULSION | −20 | NONE | — | YES | NO | YELLOW | 0.50 | 6.48 |
| DIARYLIDE YELLOW 14 | STYRENE BUTADIENE LATEX EMULSION | −20 | NONE | — | YES | NO | YELLOW | 0.98 | 8.80 |
| DIARYLIDE YELLOW 14 | ACRYLIC EMULSION POLYMER | −10 | NONE | — | NO | YES | YELLOW | 0.85 | 11.23 |
| DIARYLIDE YELLOW 14 | POLYURETHANE DISPERSION | −30 | NONE | — | YES | NO | YELLOW | 0.33 | 12.53 |
| DIARYLIDE YELLOW 14 | POLYURETHANE DISPERSION | −30 | NONE | — | YES | NO | YELLOW | 0.62 | 14.29 |
| DIARYLIDE YELLOW 14 | ACRYLIC EMULSION POLYMER | −10 | NONE | — | NO | YES | YELLOW | 1.01 | 14.92 |
| DIARYLIDE YELLOW 14 | POLYURETHANE DISPERSION | −30 | NONE | — | YES | YES | YELLOW | 0.86 | 17.51 |
| DIARYLIDE YELLOW 14 | POLYURETHANE DISPERSION | −30 | NONE | — | YES | NO | YELLOW | 0.93 | 19.71 |
| DIARYLIDE YELLOW 14 | STYRENE BUTADIENE LATEX EMULSION | −20 | NONE | — | YES | NO | YELLOW | 1.21 | 19.90 |
| DIARYLIDE | POLYURETHANE DISPERSION | −30 | NONE | — | YES | NO | YELLOW | 1.11 | 24.23 |

TABLE VIII-continued

RUB-OFF RESISTANCE OF PAPER TOWEL SUBSTRATES PRINTED WITH
YELLOW INK COMPOSITIONS OF THIS INVENTION

| (1) PIGMENT COLOR | (2) TYPE BINDER | (3) APPROX. $T_g$ OF BINDER (° C.) | (4) CROSS-LINKING AGENT | (5) CROSS-LINKING AGENT AMOUNT | (6) CONTAINS WAX | (7) HEATED TO 135° C. | (8) DENSITO-METER COLOR | (9) DEN-SITY | (10) $\Sigma\Delta E$ |
|---|---|---|---|---|---|---|---|---|---|
| YELLOW 14 DIARYLIDE | ETHYLENE VINYL ACETATE EMULSION | +10 | NONE | — | YES | YES | YELLOW | 1.08 | 27.90 |
| YELLOW 14 DIARYLIDE | ETHYLENE VINYL ACETATE EMULSION | +10 | NONE | — | YES | NO | YELLOW | 0.51 | 28.41 |
| YELLOW 14 DIARYLIDE | ETHYLENE VINYL ACETATE EMULSION | +10 | NONE | — | YES | NO | YELLOW | 1.11 | 29.11 |
| YELLOW 14 DIARYLIDE | ETHYLENE VINYL ACETATE EMULSION | +10 | KYMENE PLUS | 6% | YES | NO | YELLOW | 1.00 | 29.99 |
| YELLOW 14 DIARYLIDE | ETHYLENE VINYL ACETATE EMULSION | +10 | NONE | — | YES | NO | YELLOW | 0.67 | 30.14 |
| YELLOW 14 DIARYLIDE | ETHYLENE VINYL ACETATE EMULSION | +10 | NONE | — | YES | NO | YELLDW | 0.98 | 31.00 |
| YELLOW 14 DIARYLIDE | ETHYLENE VINYL ACETATE EMLLSION | +10 | KYMENE PLUS | 6% | YES | NO | YELLOW | 0.51 | 32.13 |
| YELLOW 14 DIARYLIDE | ETHYLENE VINYL ACETATE EMULSION | +10 | KYMENE PLUS | 6% | YES | NO | YELLOW | 0.86 | 36.69 |
| YELLOW 14 DIARYLIDE | ETHYLENE VINYL ACETATE EMULSION | +10 | NONE | — | YES | NO | YELLOW | 0.87 | 37.91 |
| YELLOW 14 DIARYLIDE | ETHYLENE VINYL ACETATE EMULSION | +10 | KYMENE PLUS | 6% | YES | NO | YELLOW | 0.64 | 40.76 |

Referring to FIGS. 4–11, the Sigma ΔE for each embodiment shown in Tables V–VIII, was plotted on a graph as a function of color density. Separate graphs were generated according to the dominant primary color of the image as indicated by the reflectance densitometer. The embodiments in Table V are plotted on the graphs shown in FIGS. 4 and 8. The embodiments in Table VI are plotted in the graphs shown in FIGS. 5 and 9. The embodiments in Table VII are plotted in the graphs shown in FIGS. 6 and 10. The embodiments in Table VIII are plotted in the graphs shown in FIGS. 7 and 11.

Samples of prior art substrates were prepared and evaluated for color density and Sigma ΔE in accordance with Procedures E, F, and G, above. For each prior art sample evaluated, a visual determination was made as to which portion of the sample exhibited high color density. The densitometer was then used to determine the area within this portion exhibiting the highest color density. This area was then selected for purposes of evaluating color density and Sigma ΔE.

For each prior art sample evaluated, Sigma ΔE (i.e.; "y(x)"), as a function of color density (i.e.; "x") was plotted according to the dominant primary color exhibited by the image as shown in the graphs of FIGS. 4–7. The Sigma ΔE as a function of color density of those prior art samples printed with process inks, was also plotted according to the dominant primary color exhibited by the image as shown in the graphs in FIGS. 8–11.

The graphs illustrated in FIGS. 4–7, compare the color density and Sigma ΔE of the current invention with the color density and Sigma ΔE of all the printed prior art substrates evaluated. The graphs illustrated in FIGS. 8–11, compare the color density and Sigma ΔE of the current invention with the color density and Sigma ΔE of prior art substrates printed with process inks.

Referring to FIGS. 4–11, polynomial inequalities are utilized to define Sigma ΔE as a function of color density for the ink compositions of the present invention as shown in FIGS. 4–11.

Figure 4:
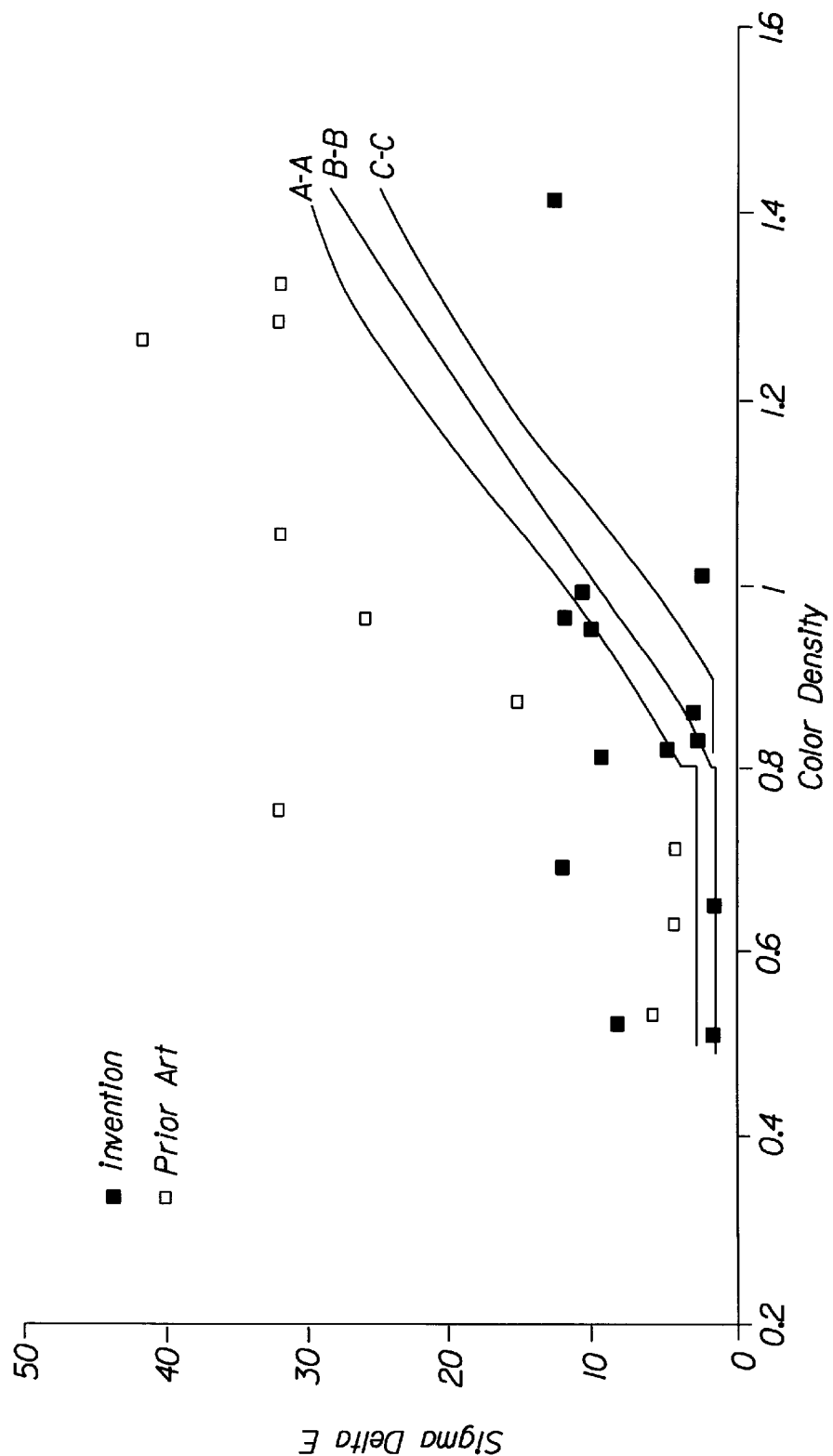
FIG. 4 is a graphical representation of Sigma ΔE plotted as a function of color density for substrates printed with inks exhibiting a dominant primary color of black.

Referring to FIG. 4, for those ink compositions of the present invention exhibiting a dominant primary color of black, Sigma ΔE is defined by the following inequality (labeled A—A in FIG. 4):

$$y(x) \leq 75.041 - 260.72x + 275.27x^2 - 70.158x^3 - 6.9911x^4,$$

wherein $0.8 \leq x \leq 1.4$, and/or, $y(x) \leq 3$, wherein $0.5 \leq x < 0.8$. Preferably, for those ink compositions of the present invention exhibiting a dominant primary color of black, Sigma ΔE is defined by the following inequality (labeled B—B in FIG. 4):

$$y(x) \leq 73.041 - 260.72x + 275.27x^2 - 70.158x^3 - 6.9911x^4,$$

wherein $0.8 \leq x \leq 1.4$, and/or, $y(x) \leq 2$, wherein $0.5 \leq x < 0.8$. More preferably, for those ink compositions of the present invention exhibiting a dominant primary color of black, Sigma ΔE is defined by the following inequality (labeled C—C in FIG. 4):

$$y(x) \leq 69.041 - 260.72x + 275.27x^2 - 70.158x^3 - 6.9911x^4,$$

wherein $0.9 \leq x \leq 1.4$, and/or, $y(x) \leq 2$, wherein $0.8 \leq x < 0.9$.

Figure 5:
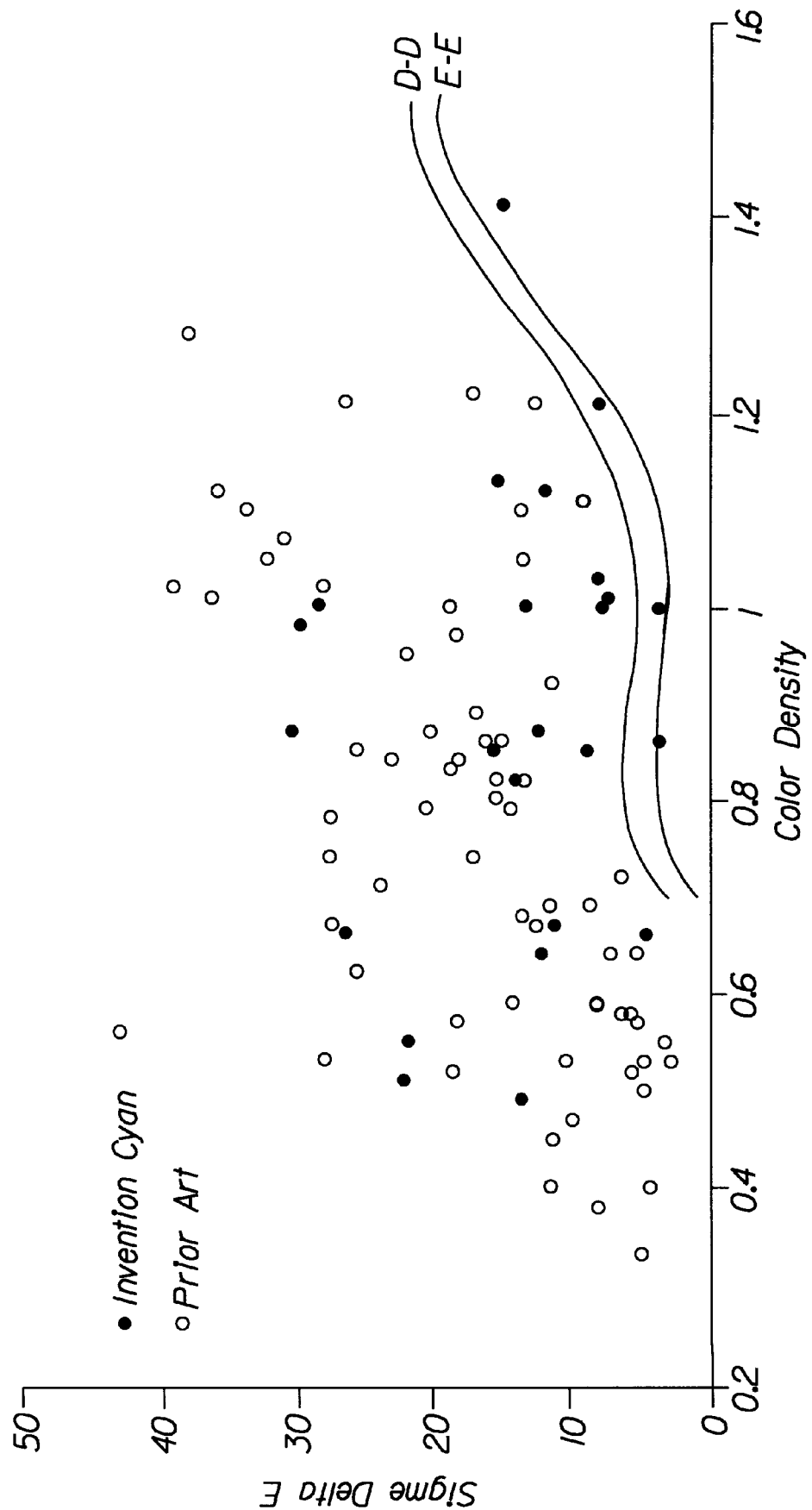
FIG. 5 is a graphical representation of Sigma ΔE plotted as a function of color density for substrates printed with inks exhibiting a dominant primary color of cyan.

Referring to FIG. 5, for those ink compositions of the present invention exhibiting a dominant primary color of cyan, Sigma ΔE is defined by the following inequality (labeled as D—D in FIG. 5):

$$y(x) \leq -593.36 + 2340.1x - 3350x^2 + 2073.8x^3 - 465.5x^4,$$

wherein $0.7 \leq x \leq 1.50$.
Preferably, for those ink compositions of the present invention exhibiting a dominant primary color of cyan, Sigma ΔE is defined by the following inequality (labeled as E—E in FIG. 5):

$$y(x) \leq -595.36 + 2340.1x - 3350x^2 + 2073.8x^3 - 465.5x^4,$$

wherein $0.7 \leq x \leq 1.50$.

Figure 6:
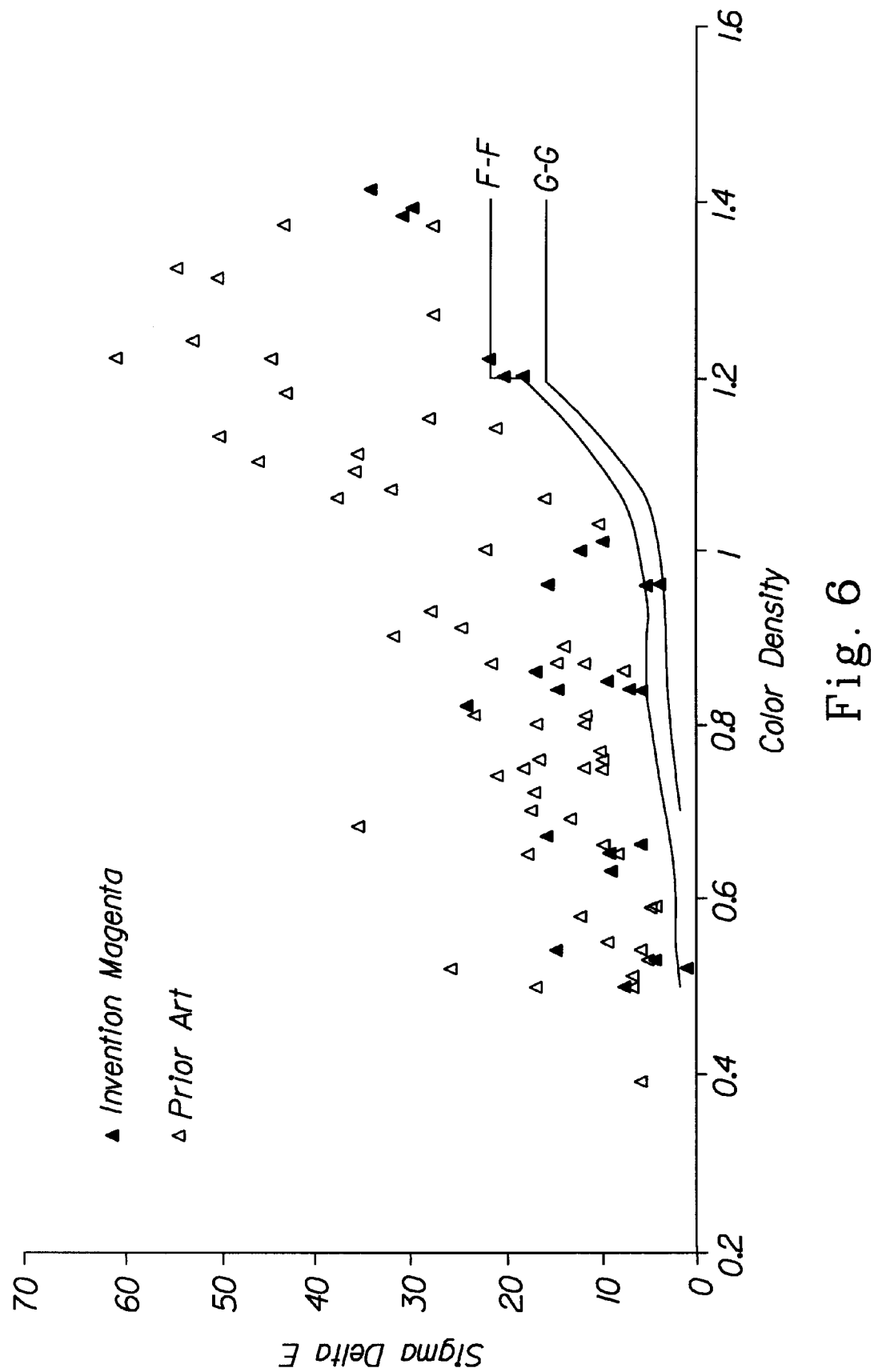
FIG. 6 is a graphical representation of Sigma ΔE plotted as a function of color density for substrates printed with inks exhibiting a dominant primary color of magenta.

Referring to FIG. 6, for those ink compositions of the present invention exhibiting a dominant primary color of magenta, Sigma ΔE is defined by the following inequality (labeled as F—F in FIG. 6):

$$y(x) \leq -1549.8 + 12473x - 40898x^2 + 69923x^3 - 65676x^4 + 32126x^5 - 6391.7x^6,$$

wherein $0.5 \leq x < 1.2$, and/or $y(x) \leq 22$, wherein $1.2 \leq x \leq 1.4$.

Preferably, for those ink compositions of the present invention exhibiting a dominant primary color of magenta, Sigma ΔE is defined by the following inequality (labeled as G—G in FIG. 6):

$$y(x) \leq -1551.8 + 12473x - 40898x^2 + 69923x^3 - 65676x^4 + 32126x^5 - 6391.7x^6,$$

wherein $0.7 \leq x < 1.2$, and/or $y(x) \leq 16$, wherein $1.2 \leq x \leq 1.4$.

Figure 7:
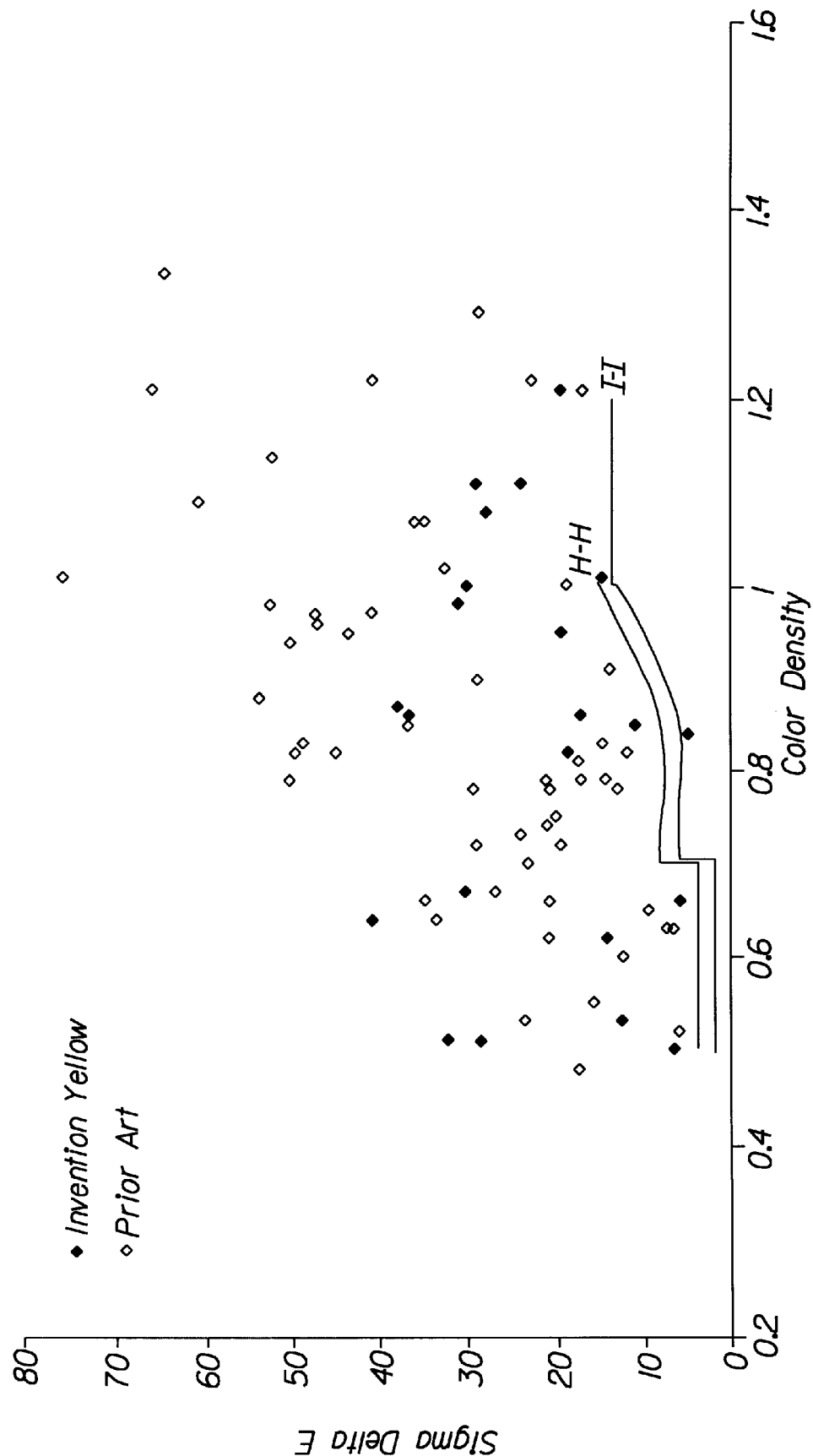
FIG. 7 is a graphical representation of Sigma ΔE plotted as a function of color density for substrates printed with inks exhibiting a dominant primary color of yellow.

Referring to FIG. 7, for those ink compositions of the present invention exhibiting a dominant primary color of yellow, Sigma ΔE is defined by the following inequality (labeled as H—H in FIG. 7):

$$y(x) \leq -2103.34 + 10184.4x - 18237x^2 + 14346.4x^3 - 4175.14x^4,$$

wherein $0.7 \leq x \leq 1.0$, and/or $y(x) \leq 4$, wherein $0.5 \leq x < 0.7$.

Preferably, for those ink compositions of the present invention exhibiting a dominant primary color of yellow, Sigma ΔE is defined by the following inequality (labeled as I—I in FIG. 7):

$$y(x) \leq -2105.34 + 10184.4x - 18237x^2 + 14346.4x^3 - 4175.14x^4,$$

wherein $0.7 \leq x < 1.0$, and/or $y(x) \leq 14$, wherein $1.0 \leq x \leq 1.2$, and/or $y(x) \leq 2$, wherein $0.5 \leq x < 0.7$.

Referring to FIGS. 8–11, the color density and Sigma ΔE of the current invention is compared with the color density and Sigma ΔE of prior art substrates printed with process inks.

Figure 8:
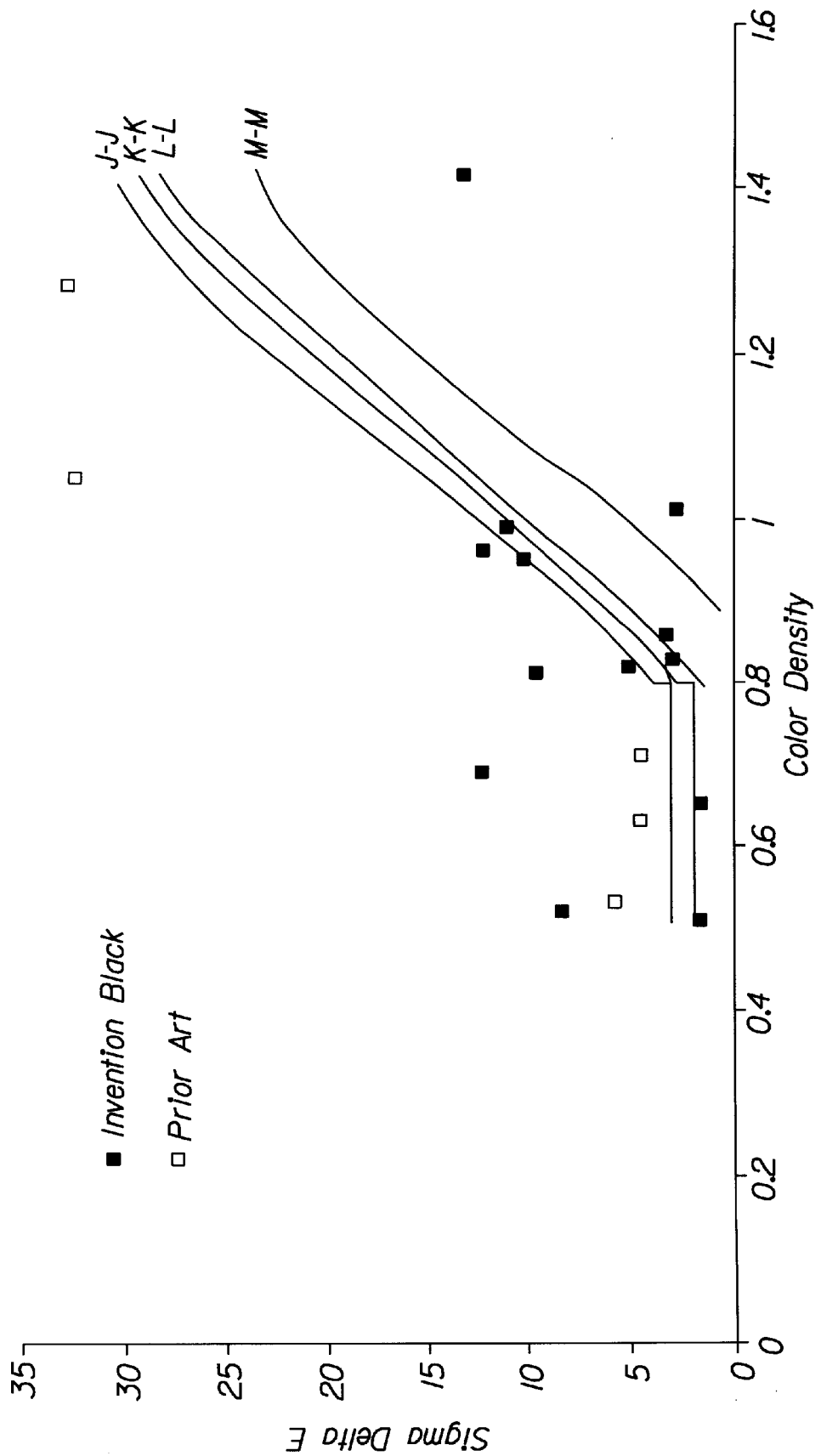
FIG. 8 is a graphical representation of Sigma ΔE plotted as a function of color density for substrates printed with process inks exhibiting a dominant primary color of black.

Referring to FIG. 8, for those ink compositions of the present invention exhibiting a dominant primary color of black, Sigma ΔE is defined by the following inequality (labeled as J—J in FIG. 8):

$$y(x) \leq 75.041 - 260.72x + 275.27x^2 - 70.158x^3 - 6.9911x^4,$$

wherein $0.8 \leq x \leq 1.4$, and/or $y \leq 3$, wherein $0.5 \leq x < 0.8$.

Preferably, for those ink compositions of the present invention exhibiting a dominant primary color of black, Sigma ΔE is defined by the following inequality (labeled as K—K in FIG. 8):

$$y(x) \leq 74.041 - 260.72x + 275.27x^2 - 70.158x^3 - 6.9911x^4,$$

wherein $0.8 \leq x \leq 1.4$, and/or $y \leq 2$, wherein $0.5 \leq x < 0.8$.

More preferably, for those ink compositions of the present invention exhibiting a dominant primary color of black, Sigma ΔE is defined by the following inequality (labeled as L—L in FIG. 8):

$$y(x) \leq 73.041 - 260.72x + 275.27x^2 - 70.158x^3 - 6.9911x^4,$$

wherein $0.8 \leq x \leq 1.4$.

Most preferably, for those ink compositions of the present invention exhibiting a dominant primary color of black, Sigma ΔE is defined by the following inequality (labeled as M—M in FIG. 8):

$$y(x) \leq 68.041 - 260.72x + 275.27x^2 - 70.158x^3 - 6.9911x^4,$$

wherein $0.9 \leq x \leq 1.4$.

Figure 9:
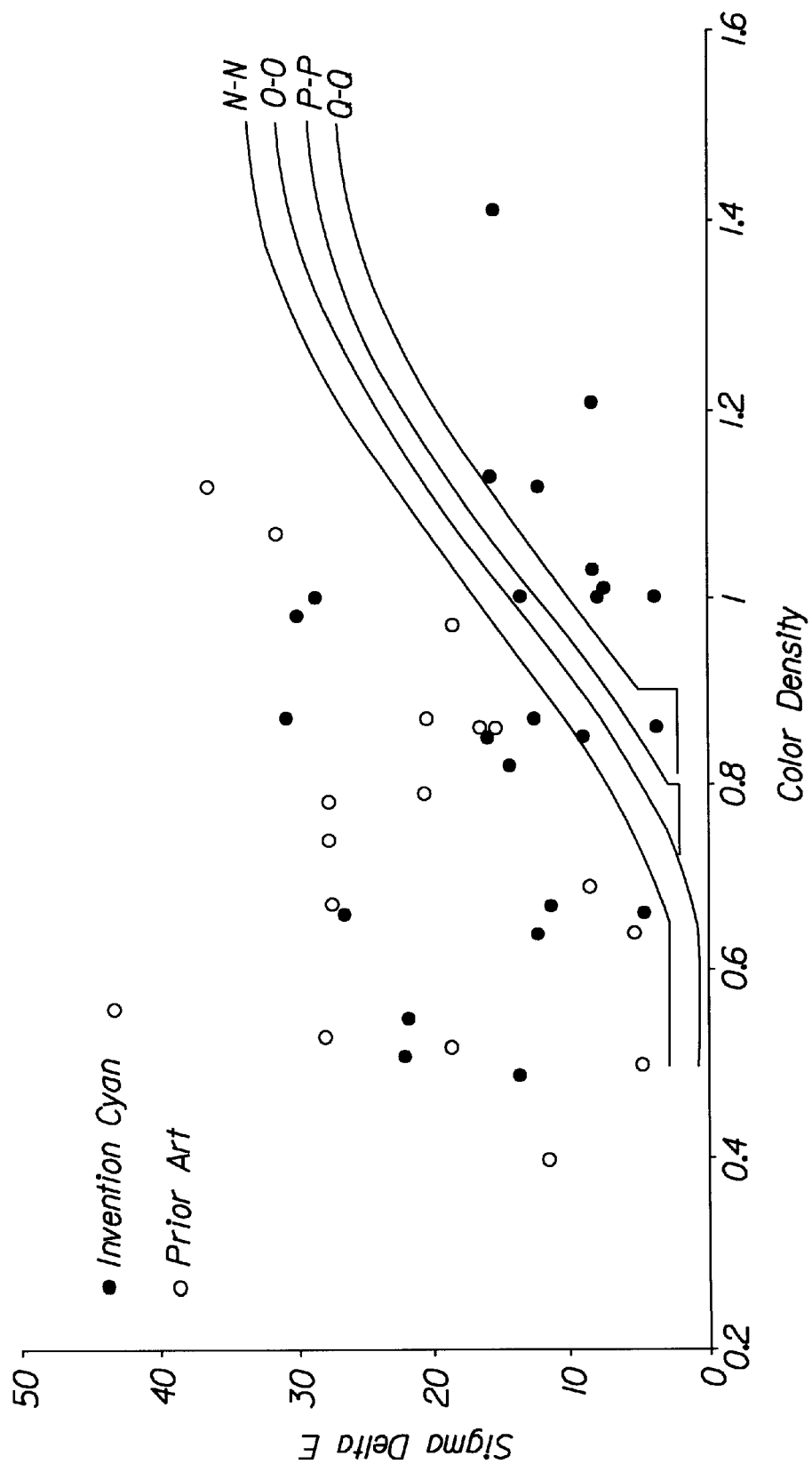
FIG. 9 is a graphical representation of Sigma ΔE plotted as a function of color density for substrates printed with process inks exhibiting a dominant primary color of cyan.

Referring to FIG. 9, for those ink compositions of the present invention exhibiting a dominant primary color of cyan, Sigma ΔE is defined by the following inequality (labeled as N—N in FIG. 9):

$$y(x) \leq 57.701 - 222.16x + 268.91x^2 - 87.964x^3,$$

wherein $0.5 \leq x \leq 1.5$.

Preferably, for those ink compositions of the present invention exhibiting a dominant primary color of cyan, Sigma ΔE is defined by the following inequality (labeled as O—O in FIG. 9):

$$y(x) \leq 55.701 - 222.16x + 268.91x^2 - 87.964x^3,$$

wherein $0.5 \leq x \leq 1.5$.

More preferably, for those ink compositions of the present invention exhibiting a dominant primary color of cyan, Sigma ΔE is defined by the following inequality (labeled as P—P in FIG. 9):

$$y(x) \leq 53.701 - 222.16x + 268.91x^2 - 87.964x^3,$$

wherein $0.8 \leq x \leq 1.5$, and/or $y(x) \leq 2$, wherein $0.7 \leq x < 0.8$.

Most preferably, for those ink compositions of the present invention exhibiting a dominant primary color of cyan, Sigma ΔE is defined by the following inequality (labeled as Q—Q in FIG. 9):

$$y(x) \leq 51.701 - 222.16x + 268.91x^2 - 87.964x^3,$$

wherein $0.9 \leq x \leq 1.5$, and/or $y(x) \leq 2$, wherein $0.8 \leq x < 0.9$.

Figure 10:
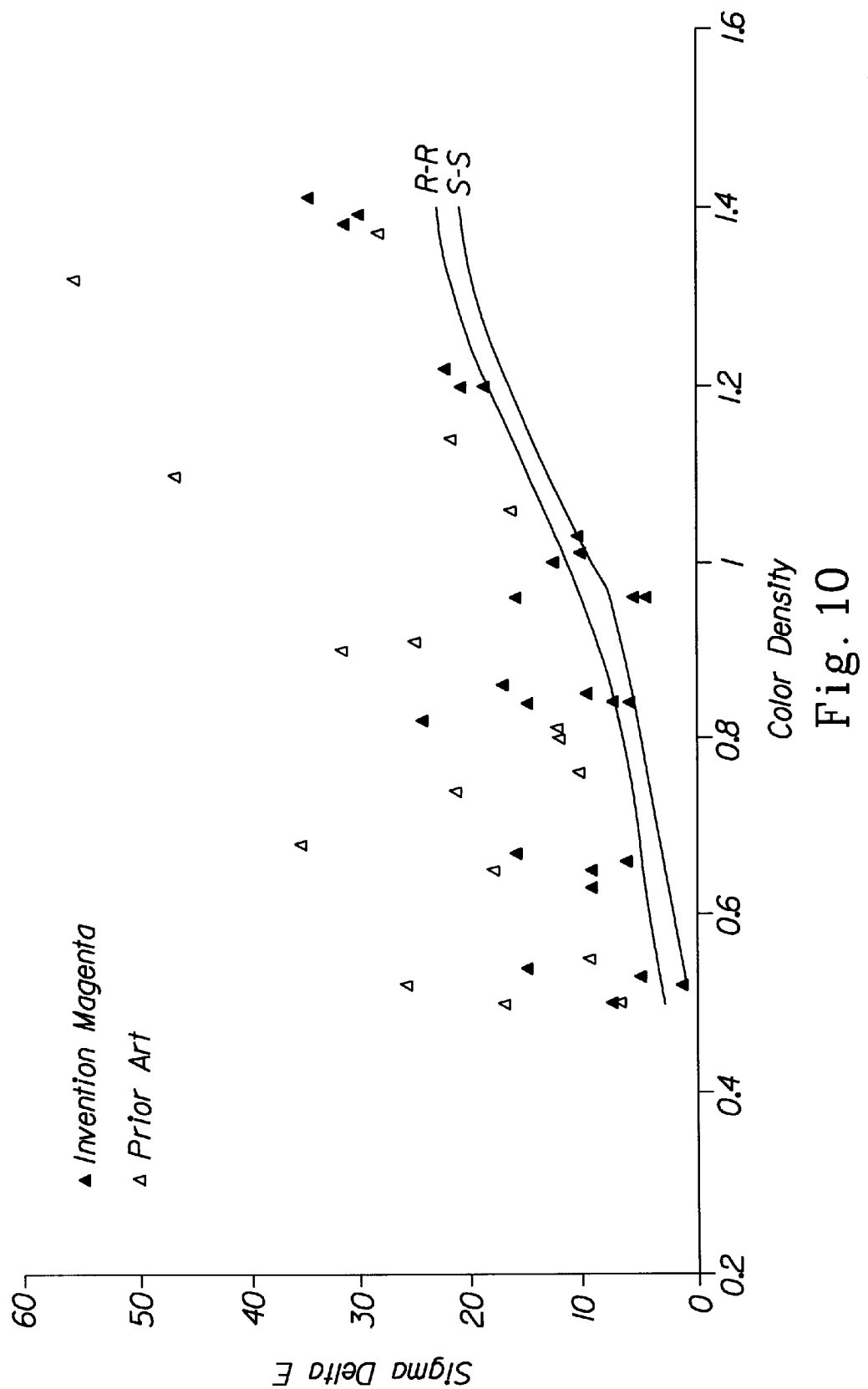
FIG. 10 is a graphical representation of Sigma ΔE plotted as a function of color density for substrates printed with process inks exhibiting a dominant primary color of magenta.

Referring to FIG. 10, for those ink compositions of the present invention exhibiting a dominant primary color of magenta, Sigma ΔE is defined by the following inequality (labeled as R—R in FIG. 10):

$$y(x) \leq -50.197 + 265.12x - 490.01x^2 + 398.49x^3 - 112.31x^4,$$

wherein $0.5 \leq x \leq 1.4$.

Preferably, for those ink compositions of the present invention exhibiting a dominant primary color of magenta, Sigma ΔE is defined by the following inequality (labeled as S—S in FIG. 10):

$$y(x) \leq -52.197 + 265.12x - 490.01x^2 + 398.49x^3 - 112.31x^4,$$

wherein $0.5 \leq x \leq 1.4$.

Figure 11:
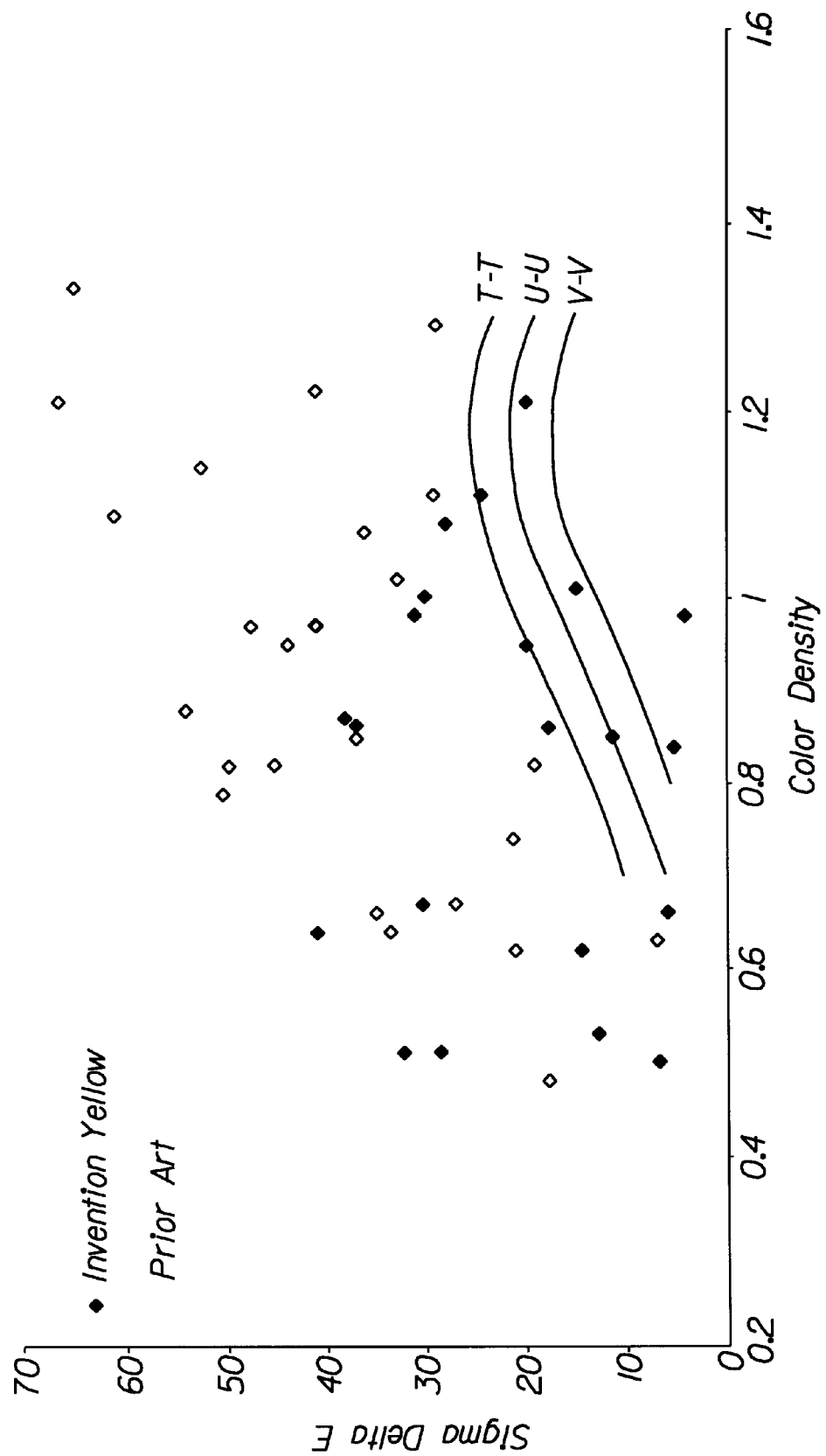
FIG. 11 is a graphical representation of Sigma ΔE plotted as a function of color density for substrates printed with process inks exhibiting a dominant primary color of yellow.

Referring to FIG. 11, for those ink compositions of the present invention exhibiting a dominant primary color of yellow, Sigma ΔE is defined by the following inequality (labeled as T—T in FIG. 11):

$$y(x) \leq 90.549 - 332.78x + 422.27x^2 - 158.5x^3,$$

wherein $0.7 \leq x < 1.3$.

Preferably, for those ink compositions of the present invention exhibiting a dominant primary color of yellow, Sigma ΔE is defined by the following inequality (labeled as U—U in FIG. 11):

$$y(x) \leq 86.549 - 332.78x + 422.27x^2 - 158.5x^3,$$

wherein $0.7 \leq x < 1.3$.

More preferably, for those ink compositions of the present invention exhibiting a dominant primary color of yellow, Sigma ΔE is defined by the following inequality (labeled as V—V in FIG. 11):

$$y(x) \leq 82.549 - 332.78x + 422.27x^2 - 158.5x^3,$$

wherein $0.8 \leq x < 1.3$.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary disposable paper product, comprising:
a fibrous sheet containing cellulose having a first outer surface, a second outer surface opposed thereto and an ink disposed on at least one of said first outer surface and said second outer surface, said ink exhibiting a dominant primary color of black, said ink having a Sigma ΔE which is a function of color density, said Sigma ΔE defined by the inequality: $y(x) \leq 75.041 - 260.72x + 275.27x^2 - 70.158x^3 - 6.9911x^4$, wherein $0.8 \leq x \leq 1.4$, and $y(x) \leq 3$, wherein $0.5 \leq x < 0.8$.

2. The sanitary disposable paper product of claim 1 said ink has a Sigma ΔE defined by the inequality: $y(x) \leq 73.041 - 260.72x + 275.27x^2 - 70.158x^3 - 6.9911x^4$, wherein $0.8 \leq x \leq 1.4$, and $y(x) \leq 2$, wherein $0.5 \leq x < 0.8$.

3. The sanitary disposable paper product of claim 1 whereby said ink comprises a process ink.

4. The sanitary disposable paper product of claim 1 wherein said ink comprises a binder selected from the group consisting of acrylic emulsion polymers, polyurethane dispersions, ethylene vinyl acetate emulsions, and styrene butadiene latex emulsions.

5. The sanitary disposable paper product of claim 4 wherein said binder is a film-forming polymer having a molecular weight of at least about 500,000.

6. The sanitary disposable paper product of claim 4 wherein said binder has a $T_g$ of less than about 100° C.

7. The sanitary disposable paper product of claim 4 wherein said binder is non-carboxylated.

8. The sanitary disposable paper product of claim 4 wherein said binder is crosslinking.

9. The sanitary disposable paper product of claim 4 wherein said ink has a binder solids to pigment solids ratio between about 0.10:1 to 3:1.

10. A sanitary disposable paper product, comprising:
a fibrous sheet containing cellulose having a first outer surface, a second outer surface opposed thereto and an ink disposed on at least one of said first outer surface and said second outer surface, said ink exhibiting a dominant primary color of cyan, said ink having a Sigma ΔE which is a function of color density, said Sigma ΔE defined by the inequality: $y(x) \leq -593.36 + 2340.1x - 3350x^2 + 2073.8x^3 - 465.5x^4$, wherein $0.7 \leq x \leq 1.50$.

11. The sanitary disposable paper product of claim 10 wherein said ink has a Sigma ΔE defined by the inequality: $y(x) \leq -595.36 + 2340.1x - 3350x^2 + 2073.8x^3 - 465.5x^4$, wherein $0.7 \leq x \leq 1.50$.

12. The sanitary disposable paper product of claim 10 wherein said ink forms an ink film having a solubility in distilled deionized water of no more than about 85 milligrams of dissolved ink pigment per gram of dry ink film.

13. The sanitary disposable paper product of claim 12 wherein said ink forms an ink film having a solubility in a solventized alkaline solution of no more than about 85 milligrams of dissolved ink pigment per gram of dry ink film.

14. A sanitary disposable paper product, comprising:
a fibrous sheet containing cellulose having a first outer surface, a second outer surface opposed thereto and an ink disposed on at least one of said first outer surface and said second outer surface, said ink exhibiting a dominant primary color of magenta, said ink having a Sigma ΔE which is a function of color density, said Sigma ΔE defined by the inequality: $y(x) \leq -1549.8 + 12473x - 40898x^2 + 69923x^3 - 65676x^4 + 32126x^5 - 6391.7x^6$, wherein $0.5 \leq x < 1.2$, and $y(x) \leq 22$, wherein $1.2 \leq x \leq 1.4$.

15. The sanitary disposable paper product of claim 14 wherein said ink has a Sigma ΔE defined by the inequality: $y(x) \leq -1551.8 + 12473x - 40898x^2 + 69923x^3 - 65676x^4 + 32126x^5 - 6391.7x^6$, wherein $0.7 \leq x < 1.2$, and $y(x) \leq 16$, wherein $1.2 \leq x \leq 1.4$.

16. The sanitary disposable paper product of claim 14 wherein said ink comprises from about 3% to 20% glycerin.

17. The sanitary disposable paper product of claim 14 wherein said ink comprises from about 0.5% to 10% wax based on weight percent solids of the total ink composition.

18. The sanitary disposable paper product of claim 14 wherein said ink composition has a pH in the range of about 7–11.

19. The sanitary disposable paper product of claim 14 wherein the raw ink of said ink composition has a Shell Cup viscosity at 20° C. of about 200 centipoise or less.

20. A sanitary disposable paper product, comprising:
a fibrous sheet containing cellulose having a first outer surface, a second outer surface opposed thereto and an ink disposed on at least one of said first outer surface and said second outer surface, said ink exhibiting a dominant primary color of yellow, said ink having a Sigma ΔE which is a function of color density, said Sigma ΔE defined by the inequality: $y(x) \leq -2103.34 + 10184.4x - 18237x^2 + 14346.4x^3 - 4175.14x^4$, wherein $0.7 \leq x \leq 1.0$, and $y(x) \leq 4$, wherein $0.5 \leq x < 0.7$.

21. The sanitary disposable paper product of claim 20 wherein said ink has a Sigma ΔE defined by the inequality: $y(x) \leq -2105.34 + 10184.4x - 18237x^2 + 14346.4x^3 - 4175.14x^4$, wherein $0.7 \leq x < 1.0$, and $y(x) \leq 14$, wherein $1.0 \leq x \leq 1.2$, and $y(x) \leq 2$, wherein $0.5 \leq x < 0.7$.

22. The sanitary disposable paper product of claim 20 wherein said ink forms an ink film having an ink film toughness measured at 50% strain of at least about 0.01 MPa.

23. The sanitary disposable paper product of claim 22 wherein said ink has an ink film toughness measured at 50% strain of at least about 0.05 MPa.

24. The sanitary disposable paper product of claim 22 wherein said ink film has a maximum strain of at least about 0.3.

25. The sanitary disposable paper product of claim 24 wherein said ink film has a maximum strain of at least about 1.

26. A sanitary disposable paper product, comprising:
a fibrous sheet containing cellulose having a first outer surface, a second outer surface opposed thereto and a process ink disposed on at least one of said first outer surface and said second outer surface, said process ink exhibiting a dominant primary color of black, said process ink having a Sigma ΔE which is a function of color density, said Sigma ΔE defined by the inequality: $y(x) \leq 75.041 - 260.72x + 275.27x^2 - 70.158x^3 - 6.9911x^4$, wherein $0.8 \leq x \leq 1.4$, and $y \leq 3$, wherein $0.5 \leq x < 0.8$.

27. The sanitary disposable paper product of claim 26 wherein said ink has a Sigma ΔE defined by the inequality: $y(x) \leq 74.041 - 260.72x + 275.27x^2 - 70.158x^3 - 6.9911x^4$, wherein $0.8 \leq x \leq 1.4$, and $y \leq 2$, wherein $0.5 \leq x < 0.8$.

28. A sanitary disposable paper product, comprising:
a fibrous sheet containing cellulose having a first outer surface, a second outer surface opposed thereto and a process ink disposed on at least one of said first outer surface and said second outer surface, said process ink exhibiting a dominant primary color of cyan, said process ink having a Sigma ΔE which is a function of color density, said Sigma ΔE defined by the inequality: $y(x) \leq 57.701 - 222.16x + 268.91x^2 - 87.964x^3$, wherein $0.5 \leq x \leq 1.5$.

29. The sanitary disposable paper product of claim 28 wherein said ink has a Sigma ΔE defined by the inequality: $y(x) \leq 55.701 - 222.16x + 268.91x^2 - 87.964x^3$, wherein $0.5 \leq x \leq 1.5$.

30. A sanitary disposable paper product, comprising:
a fibrous sheet containing cellulose having a first outer surface, a second outer surface opposed thereto and a process ink disposed on at least one of said first outer surface and said second outer surface, said process ink exhibiting a dominant primary color of magenta, said process ink having a Sigma ΔE which is a function of said color density, said Sigma ΔE defined by the inequality: $y(x) \leq -50.197 + 265.12x - 490.01x^2 + 398.49x^3 - 112.31x^4$, wherein $0.5 \leq x \leq 1.4$.

31. The sanitary disposable paper product of claim 30 wherein said ink has a Sigma ΔE defined by the inequality: $y(x) \leq -52.197 + 265.12x - 490.01x^2 + 398.49x^3 - 112.31x^4$, wherein $0.5 \leq x \leq 1.4$.

32. A sanitary disposable paper product, comprising:
a fibrous sheet, containing cellulose having a first outer surface, a second outer surface opposed thereto and a process ink disposed on at least one of said first outer surface and said second outer surface, said process ink exhibiting a dominant primary color of yellow, said process ink having a Sigma ΔE which is a function of said color density, said Sigma ΔE defined by the inequality: $y(x) \leq 90.549 - 332.78x + 422.27x^2 - 158.5x^3$, wherein $0.7 \leq x < 1.3$.

33. The sanitary disposable paper product of claim 32 wherein said ink has a Sigma ΔE defined by the inequality: $y(x) \leq 86.549 - 332.78x + 422.27x^2 - 158.5x^3$, wherein $0.7 \leq x < 1.3$.

* * * * *